(12) United States Patent
Belelie et al.

(10) Patent No.: US 7,259,275 B2
(45) Date of Patent: *Aug. 21, 2007

(54) METHOD FOR PREPARING CURABLE AMIDE GELLANT COMPOUNDS

(75) Inventors: Jennifer L. Belelie, Oakville (CA); Adela Goredema, Mississauga (CA); Peter G. Odell, Mississauga (CA); Eniko Toma, Mississauga (CA)

(73) Assignee: Xerox Corporation, Stamford, CT (US)

( * ) Notice: Subject to any disclaimer, the term of this patent is extended or adjusted under 35 U.S.C. 154(b) by 45 days.

This patent is subject to a terminal disclaimer.

(21) Appl. No.: 11/290,328

(22) Filed: Nov. 30, 2005

(65) Prior Publication Data

US 2007/0123724 A1 May 31, 2007

(51) Int. Cl.
C07C 229/00 (2006.01)
(52) U.S. Cl. .................. 560/169; 554/37; 564/153
(58) Field of Classification Search ................ 560/169; 554/37; 564/153
See application file for complete search history.

(56) References Cited

U.S. PATENT DOCUMENTS

| | | | |
|---|---|---|---|
| 3,653,932 | A | 4/1972 | Berry et al. |
| 4,390,369 | A | 6/1983 | Merritt et al. |
| 4,484,948 | A | 11/1984 | Merritt et al. |
| 4,684,956 | A | 8/1987 | Ball |
| 4,851,045 | A | 7/1989 | Taniguchi |
| 4,889,560 | A | 12/1989 | Jaeger et al. |
| 4,889,761 | A | 12/1989 | Titterington et al. |
| 5,006,170 | A | 4/1991 | Schwarz et al. |
| 5,151,120 | A | 9/1992 | You et al. |
| 5,221,335 | A | 6/1993 | Williams et al. |
| 5,372,852 | A | 12/1994 | Titterington et al. |
| 5,496,879 | A | 3/1996 | Griebel et al. |
| 5,621,022 | A | 4/1997 | Jaeger et al. |
| 5,804,671 | A | 9/1998 | Dones et al. |
| 5,889,076 | A | 3/1999 | Dones et al. |
| 6,239,189 | B1 | 5/2001 | Narayan et al. |
| 6,316,517 | B1 | 11/2001 | Dones et al. |
| 6,467,897 | B1 | 10/2002 | Wu et al. |
| 6,586,492 | B1 | 7/2003 | Caiger et al. |
| 6,896,937 | B2 | 5/2005 | Woudenberg |
| 2003/0036587 | A1 | 2/2003 | Kozak |

FOREIGN PATENT DOCUMENTS

| | | |
|---|---|---|
| EP | 0206286 B1 | 5/1990 |
| EP | 0187352 B1 | 6/1991 |
| WO | WO94/04619 | 3/1994 |

OTHER PUBLICATIONS

Copending U.S. Appl. No. 11/289,882, filed Nov. 30, 2005.*

Copending U.S. Appl. No. 11/018,378, filed Dec. 22, 2004, entitled "Curable Phase Change Ink Composition," by Peter G. Odell et al.

Copending U.S. Appl. No. 11/004,761, filed Dec. 4, 2004, entitled "Curable Trans-1,2-Cyclohexane Bis[urea-urethane] Compounds," by Rina Carlini et al.

Copending U.S. Appl. No. 11/181,632, filed Jul. 13, 2005, entitled "Ink Carriers, Phase Change Inks Including Same and Methods for Making Same," by Adela Goredema et al.

Copending U.S. Appl. No. (not yet assigned), filed concurrently herewith, entitled "Phase Change Inks Containing Curable Isocyanate-Derived Compounds," by Jeffery H. Banning et al.

Copending U.S. Appl. No. (not yet assigned), filed concurrently herewith, entitled "Phase Change Inks Containing Curable Isocyanate-Derived Compounds and Phase Change Inducing Components," by Jennifer L. Belelie et al.

(Continued)

*Primary Examiner*—Johann Richter
*Assistant Examiner*—Sudhakar Katakam
(74) *Attorney, Agent, or Firm*—Judith L. Byorick

(57) ABSTRACT

Disclosed is a process for preparing a compound of the formula

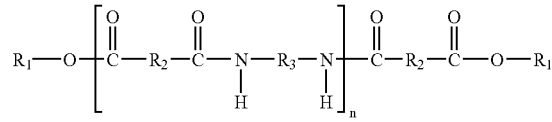

wherein $R_1$ is an alkyl group having at least one ethylenic unsaturation, an arylalkyl group having at least one ethylenic unsaturation, or an alkylaryl group having at least one ethylenic unsaturation, $R_2$ and $R_3$ each, independently of the others, are alkylene groups, arylene groups, arylalkylene groups, or alkylarylene groups, and n is an integer representing the number of repeat amide units and is at least 1, said process comprising: (a) reacting a diacid of the formula

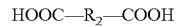

with a diamine of the formula

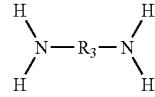

in the absence of a solvent while removing water from the reaction mixture to form an acid-terminated oligoamide intermediate; and (b) reacting the acid-terminated oligoamide intermediate with a monoalcohol of the formula

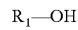

in the presence of a coupling agent and a catalyst to form the product.

27 Claims, No Drawings

OTHER PUBLICATIONS

Copending U.S. Appl. No. (not yet assigned), filed concurrently herewith, entitled "Phase Change Inks Containing Compounds Derived from Isocyanate, Unsaturated Alcohol, and Polyol," with the named inventors Jennifer L. Belelie, Rina Carlini.

Copending U.S. Appl. No. (not yet assigned), filed concurrently herewith, entitled "Radiation Curable Phase Change Inks Containing Curable Epoxy-Polyamide Composite Gellants," by Rina Carlini et al.

Copending U.S. Appl. No. (not yet assigned), filed concurrently herewith, entitled "Radiation Curable Phase Change Inks Containing Gellants," by Peter G. Odell et al.

Copending U.S. Appl. No. (not yet assigned), filed concurrently herewith, entitled "Phase Change Inks," by Peter Gordon Odell et al.

Copending U.S. Appl. No. (not yet assigned), filed concurrently herewith, entitled "Phase Change-Inks and Methods for Making Same," by Adela Goredema et al.

Copending U.S. Appl. No. (not yet assigned), filed concurrently herewith, entitled "Ink Carriers Containing Nanoparticles, Phase Change Inks Including Same and Methods for Making Same," by Marcel P. Breton et al.

Copending U.S. Appl. No. (not yet assigned), filed concurrently herewith, entitled "Black Inks and Method for Making Same," by Marcel P. Breton et al.

Copending U.S. Appl. No. (not yet assigned), filed concurrently herewith, entitled "Ink Carriers, Phase Change Inks Includng Same and Methods for Making Same," by Marcel P. Breton et al.

Copending U.S. Appl. No. (not yet assigned), filed concurrently herewith, entitled "Curable Overcoat for Wax-Based Inks," by Jennifer L. Belelie et al.

Copending U.S. Appl. No. (not yet assigned), filed concurrently herewith, entitled "Radiation Curable Ink Containing a Curable Wax," by Jennifer Lynne Belelie et al.

Copending U.S. Appl. No. (not yet assigned), filed concurrently herewith, entitled "Curable Phase Change Compositions and Methods for Using Such Compositions," by Jennifer L. Belelie et al.

Copending U.S. Appl. No. (not yet assigned), filed concurrently herewith, entitled "Overcoat Compositions, Oil-Based Ink Compositions, and Processes for Ink-Jet Recording Using Overcoat Compositions and Oil-Based Ink Compositions," by Gregory J. Kovacs et al.

Copending U.S. Appl. No. (not yet assigned), filed concurrently herewith, entitled "Pre-Treatment Compositions, Oil-Based Ink Compositions, and Processes for Ink-Jet Recording Using Pre-Treatment Compositions and Oil-Based Ink Compositions," by Gregory J. Kovacs et al.

Copending U.S. Appl. No. (not yet assigned), filed concurrently herewith, entitled "Curable Amide Gellant Compounds," by Eniko Toma et al.

Copending U.S. Appl. No. (not yet assigned), filed concurrently herewith, entitled "Phase Change Inks Containing Curable Amide Gellant Compounds," by Eniko Toma et al.

Copending U.S. Appl. No. (not yet assigned), filed concurrently herewith, entitled "Process for Making Curable Amide Gellant Compouds," by Eniko Toma et al.

Copending U.S. Appl. No. (not yet assigned), filed concurrently herewith, entitled "Photoinitiator With Phase Properties and Gellant Affinity," by Peter G. Odell et al.

Copending U.S. Appl. No. (not yet assigned), filed concurrently herewith, entitled "Phase Change Inks Containing Photoinitiator With Phase Change Properties and Gellant Affinity," by Peter G. Odell et al.

English abstract for German Patent Publication DE 4205636AL.

English abstract for German Patent Publication DE 4205713AL.

* cited by examiner

METHOD FOR PREPARING CURABLE AMIDE GELLANT COMPOUNDS

CROSS-REFERENCE TO RELATED APPLICATIONS

Copending Application U.S. Ser. No. 11/018,378, filed Dec. 22, 2004, entitled "Curable Phase Change Ink Composition," with the named inventors Peter G. Odell, Marcel P. Breton, Christine E. Bedford, and Chris A. Wagner, the disclosure of which is totally incorporated herein by reference, discloses ink compositions that comprise one or more radiation curable oil soluble components and one or more thermal solvents, as well as methods of preparing such ink compositions and methods of using such ink compositions.

Copending Application U.S. Ser. No. 11/004,761, filed Dec. 4, 2004, entitled "Curable Trans-1,2-Cyclohexane Bis [urea-urethane] Compounds," with the named inventors Rina Carlini, Eniko Toma, Peter G. Odell, and Jeffery H. Banning, the disclosure of which is totally incorporated herein by reference, discloses curable trans-1,2-cyclohexane bis[urea-urethane] compounds of the formulae

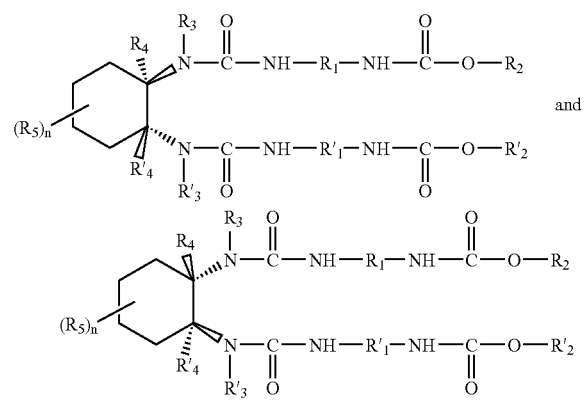

and wherein $R_1$ and $R'_1$ each, independently of the other, are alkylene, arylene, arylalkylene, or alkylarylene groups, $R_2$ and $R'_2$ each, independently of the other, are alkyl, aryl, arylalkyl, or alkylaryl groups, $R_3$ and $R'_3$ each, independently of the other, are hydrogen atoms or alkyl groups, $R_4$ and $R'_4$ each, independently of the other, are hydrogen atoms, fluorine atoms, alkyl groups, or phenyl groups, n is an integer of 0, 1, 2, 3, or 4, and $R_5$ is an alkyl, aryl, arylalkyl, or alkylaryl group, or a substituent other than an alkyl, aryl, arylalkyl, or alkylaryl group, provided that at least one of $R_1$, $R'_1$, $R_2$, $R'_2$, $R_3$, $R'_3$, $R_4$, $R'_4$, or one or more of $R_5$ is an alkyl, alkylene, arylalkyl, arylalkylene, alkylaryl, or alkylarylene group containing an ethylenic unsaturation rendering the compound curable upon exposure to heat and/or actinic radiation.

Copending Application U.S. Ser. No. 11/181,632, filed Jul. 13, 2005, entitled "Ink Carriers, Phase Change Inks Including Same and Methods for Making Same," with the named inventors Adela Goredema, Christine E. Bedford, Marcel P. Breton, and Chris A. Wagner, the disclosure of which is totally incorporated herein by reference, discloses an ink carrier comprising an ester terminated oligo-amide material having a substantially low polydispersity. This ink carrier can be combined with a colorant to produce an ink composition.

Copending Application U.S. Ser. No. 11/289,931, filed concurrently herewith, entitled "Phase Change Inks Containing Curable Isocyanate-Derived Compounds," with the named inventors Jeffery H. Banning, Jennifer L. Belelie, Peter G. Odell, Rina Carlini, Jule W. Thomas, Donald R. Titterington, Paul F. Smith, Stephan V. Drappel, and Christopher A. Wagner, the disclosure of which is totally incorporated herein by reference, discloses a phase change ink comprising a colorant, an initiator, and a phase change ink carrier, said carrier comprising (A) a urethane which is the reaction product of a mixture comprising (1) an isocyanate; and (2) an alcohol selected from the group consisting of 1,4 butanediol vinyl ether, 2-allyloxy ethanol, 1,4-cyclohexanedimethanol vinyl ether, ethylene glycol vinyl ether, di(ethylene glycol) vinyl ether, and mixtures thereof; (B) a compound which is the reaction product of a mixture comprising (1) an isocyanate; and (2) a component comprising (a) an amine having at least one ethylenic unsaturation; (b) an acid having at least one ethylenic unsaturation; (c) a mixture of an amine having at least one ethylenic unsaturation and an alcohol having at least one ethylenic unsaturation; (d) a mixture of an acid having at least one ethylenic unsaturation and an alcohol having at least one ethylenic unsaturation; or (e) mixtures thereof; or (C) a mixture of (A) and (B); said ink being curable upon exposure to ultraviolet radiation.

Copending Application U.S. Ser. No. 11/290,098, filed concurrently herewith, entitled "Phase Change Inks Containing Curable Isocyanate-Derived Compounds and Phase Change Inducing Components," with the named inventors Jennifer L. Belelie, Peter G. Odell, Marcel P. Breton, Jeffery H. Banning, Stephan V. Drappel, and Christopher A. Wagner, the disclosure of which is totally incorporated herein by reference, discloses a phase change ink comprising a colorant, an initiator, and a phase change ink carrier, said carrier comprising (A) a compound which is the reaction product of a mixture comprising (1) an isocyanate; and (2) a component comprising (a) an alcohol having at least one ethylenic unsaturation; (b) an amine having at least one ethylenic unsaturation; (c) an acid having at least one ethylenic unsaturation; or (d) mixtures thereof, (B) a phase change inducing component, said phase change inducing component containing at least one hydroxyl group, said phase change inducing component having a melting point of about 40° C. or higher, and (C) an optional curable viscosity modifying ester, said ink being curable upon exposure to ultraviolet radiation.

Copending Application U.S. Ser. No. 11/289,883, filed concurrently herewith, entitled "Phase Change Inks Containing Compounds Derived from Isocyanate, Unsaturated Alcohol, and Polyol," with the named inventors Jennifer L. Belelie, Rina Carlini, and Eniko Toma, the disclosure of which is totally incorporated herein by reference, discloses a phase change ink comprising a colorant, an initiator, and a phase change ink carrier, said carrier comprising (A) a first isocyanate-derived compound which is the reaction product of a mixture comprising (1) an isocyanate; and (2) a component comprising (a) an alcohol having at least one ethylenic unsaturation; (b) an amine having at least one ethylenic unsaturation; (c) an acid having at least one ethylenic unsaturation; or (d) mixtures thereof, (B) a second isocyanate-derived compound which is the reaction product of (1) a diisocyanate; (2) a monoalcohol having exactly one hydroxyl group and having at least one ethylenic unsaturation; and (3) a polyol having two or more hydroxyl groups, (C) an optional phase change inducing component, said phase change inducing component containing at least one hydroxyl group, said phase change inducing component having a melting point of about 40° C. or higher, and (D) an optional curable viscosity modifying ester, said ink being curable upon exposure to ultraviolet radiation.

Copending Application U.S. Ser. No. 11/289,473, filed concurrently herewith, entitled "Radiation Curable Phase Change Inks Containing Curable Epoxy-Polyamide Composite Gellants," with the named inventors Rina Carlini, Eniko Toma, Peter G. Odell, and Vaisnavi Siritharan, the disclosure of which is totally incorporated herein by reference, discloses a radiation curable phase change ink preferably used in piezoelectric ink jet devices including an ink vehicle that includes at least one curable epoxypolyamide gellant, and at least one colorant. The use of the gellant enables the ink to form a gel state having a viscosity of at least $10^3$ mPa·s at very low temperatures of about 25° C. to about 100° C. The ink may thus be jetted, for example onto an intermediate transfer member surface or directly to an image receiving substrate, at very low jetting temperatures of, for example, about 40° C. to about 110° C. In a preferred method of forming an image with the ink, the ink is heated to a first temperature at which the ink may be jetted, jetted onto an image receiving or intermediate transfer member surface maintained at a second temperature at which the ink forms a gel state, if appropriate subsequently transferred from the intermediate transfer member surface to an image receiving substrate, and exposed to radiation energy to cure the curable components of the ink.

Copending Application U.S. Ser. No. 11/289,609, filed concurrently herewith, entitled "Radiation Curable Phase Change Inks Containing Gellants," with the named inventors Peter G. Odell, C. Geoffrey Allen, Christopher A. Wagner, Stephan V. Drappel, Rina Carlini, and Eniko Toma, the disclosure of which is totally incorporated herein by reference, discloses a radiation curable phase change ink preferably used in piezoelectric ink jet devices including an ink vehicle that includes at least one gellant comprising a curable polyamide-epoxy acrylate component and a polyamide component, and at least one colorant, The use of the gellant enables the ink to form a gel state having a viscosity of at least $10^3$ mPa·s at very low temperatures of about 25° C. to about 100° C. The ink may thus be jetted at very low jetting temperatures of, for example, about 40° C. to about 110° C. The ink may be used to form an image by heating the ink to a first temperature at which the ink may be jetted, jetting onto a member or substrate maintained at a second temperature at which the ink forms a gel state, and exposing the ink to radiation energy to polymerize curable components of the ink.

Copending Application U.S. Ser. No. 11/289,620, filed concurrently herewith, entitled "Phase Change Inks," with the named inventors Peter Gordon Odell, Paul F. Smith, Jennifer Lynne Belelie, Eniko Toma, Stephan Drappel, C. Geoffrey Allen, Rina Carlini, and Christopher A. Wagner, the disclosure of which is totally incorporated herein by reference, discloses a phase change ink having a viscosity of from about 4 mPa-s to about 50 mPa-s at a first temperature and a viscosity of from $10^4$ mPa-s to about $10^9$ mPa-s at a second lower temperature. The second temperature may be below the first temperature by at least 10° C., but by no more than 50° C. The first temperature may be from about 60° C. to about 110° C. and the second temperature may be from about 20° C. to about 70° C. A curve of $\log_{10}$ viscosity of the phase change ink plotted against temperature in degrees Celsius may have a slope having an absolute value less than 0.02 at the first temperature and have a slope having an absolute value greater than 0.08 for at least a region between the first and second temperatures.

Copending Application U.S. Ser. No. 11/291,592, filed concurrently herewith, entitled "Phase Change Inks and Methods for Making Same," with the named inventors Adela Goredema, Christine E. Bedford, Marcel P. Brenton, and Christopher A. Wagner, the disclosure of which is totally incorporated herein by reference, discloses a phase change ink composition and a method for forming the ink composition. The phase change ink composition comprises (1) an ink carrier comprising (A) a first component which comprises a monoester wax or blend of monoesters having at least one alkyl group comprising at least 10 carbon atoms, and (B) a second component which comprises a polyalkylene wax, and (2) a urea gellant, and (3) a colorant.

Copending Application U.S. Ser. No. 11/291,540, filed concurrently herewith, entitled "ink Carriers Containing Nanoparticles, Phase Change Inks including Same and Methods for Making Same," with the named inventors Marcel P. Breton, Adela Goredema, Christine E. Bedford, Christopher A. Wagner, Sandra Gardner, Nan-Xing Hu, and Bruce Goodbrand, the disclosure of which is totally incorporated herein by reference, discloses an ink carrier and a method for forming same, and a phase change ink including same. The ink carrier comprises a colloidal dispersion of at least one of silica nanoparticies and metal oxide particles. The ink carrier can also include a low melting wax, and a gelling agent The ink carrier exhibits a substantially uniform distribution of the nanoparticles so that they are discretely distributed therewithin, and are substantially resistant to the aggregation of the nanoparticles distributed therewithin.

Copending Application U.S. Ser. No. 11/291,283, filed concurrently herewith, entitled "Black Inks and Method for Making Same," with the named inventors Marcel P. Breton, Raymond W. Wong, Christine E. Bedford, Christopher A. Wagner, and Caroline Turek, the disclosure of which is totally incorporated herein by reference, discloses a phase change black ink composition comprising (1) a low polarity ink carrier comprising (A) an ester-terminated polyamide, (B) a Guerbet alcohol or a Guerbet alcohol mixture containing at least one linear alcohol, and (C) a low polarity wax, and (2) a black colorant. The ink carrier can also contain a dispersant. The ink is resistant to aggregation and settling of the black colorant when a standby-mode printer temperature for the ink is not more than about the gel temperature of the ink.

Copending Application U.S. Ser. No. 11/291,315, filed concurrently herewith, entitled "Ink Carriers, Phase Change Inks Including Same and Methods for Making Same," with the named inventors Marcel P. Breton, Adela Goredema, Christine E. Bedford, Christopher A. Wagner, Stephan Drappel, Caroline Turek, Raymond W. Wong, and Nadia Edun, the disclosure of which is totally incorporated herein by reference, discloses an ink carrier comprising (A) an antioxidant mixture comprising (a) a hindered phenol antioxidant and (b) a hindered amine antioxidant (B) a polyalkylene wax, (C) a functional wax and (D) an ester-terminated amide. The low polarity ink carrier is substantially resistant to phase separation, has excellent thermal stability, resists autocatalylic dagradation of the ink composition and a substantial color shift upon standing and provides enhanced humidity resistance. This ink carrier can be combined with a colorant to produce an ink composition.

Copending Application U.S. Ser. No. 11/289,552, filed concurrently herewith, entitled "Curable Overcoat for Wax-Based Inks," with the named inventors Jennifer L. Belelie and Peter G. Odell, the disclosure of which is totally incorporated herein by reference, discloses an ink jettable overprint composition including at least one of a polymerizable monomer and/or a polymerizable oligomer; at least one photoinitiator; and at least one wax.

Copending Application U.S. Ser. No. 11/289,615, filed concurrently herewith, entitled "Radiation Curable ink Containing a Curable Wax", with the named inventors Jennifer Lynne Belelie, Peter Gordon Odell, Christopher A. Wagner, and C. Geoffrey Allen, the disclosure of which is totally incorporated herein by reference, discloses a curable monomer that is liquid at 25° C., a curable wax and a colorant together forming a radiation curable ink. This ink may be used to form images by providing the radially curable ink at a first temperature; applying the radiation curable ink to the substrate to form an image, the substrate being at a second temperature, which is below the first temperature; and exposing the radiation curable ink to radiation to cure the ink.

Copending Application U.S. Ser. No. 11/289,521, filed concurrently herewith, entitled "Curable Phase Change Compositions and Methods for Using Such Compositions," with the named inventors Jennifer L. Belelie, Peter G. Odell, Daryl Vanbesien, and Marcel P. Breton, the disclosure of which is totally incorporated herein by reference, discloses a phase change, curable composition comprising curable monomer, photoinitiator that initiates polymerization of the curable monomer, and phase change agent that provides the composition with an increase in viscosity of at least four orders of magnitude, from a first temperature, the first temperature being from 50° C. to 130° C., to a second temperature, the second temperature being from 0° C. to 70° C., wherein the second temperature is at least 10° C. below the first temperature. A coating over an image may be applied by providing a composition comprising curable monomer at a first temperature; applying the composition over the image, the image being at a second temperature; and exposing the composition to radiation to initiate polymerization of the curable monomer. In this process, the composition has a viscosity at the second temperature that is at least four orders of magnitude greater than its viscosity at the first temperature.

Copending Application U.S. Ser. No. 11/289,605, filed concurrently herewith, entitled "Overcoat Compositions, Oil-Based Ink Compositions, and Processes for Ink-Jet Recording Using Overcoat Compositions and Oil-Based Ink Compositions," with the named inventors Gregory J. Kovacs and Marcel P. Breton, the disclosure of which is totally incorporated herein by reference, discloses overcoat compositions including film-forming resins and organic liquids. Overcoat compositions are included in ink sets that also include oil-based ink compositions. Methods for ink-jet printing use oil-based ink compositions and overcoat compositions.

Copending Application U.S. Ser. No. 11/289,573, filed concurrently herewith, entitled "Pre-Treatment Compositions, Oil-Based Ink Compositions, and Processes for Ink-Jet Recording Using Pre-Treatment Compositions and Oil-Based Ink Compositions," with the named inventors Gregory J. Kovacs and Marcel P. Breton, the disclosure of which is totally incorporated herein by reference, discloses pre-treatment compositions including organic liquids and cross-linking initiators. Pre-treatment compositions are included in ink sets that also include oil-based ink compositions. Oil-based ink compositions include organic liquids, unsaturated fatty materials having terminal polar functional groups, colorants, and metal salts. Methods for ink-jet printing use pre-treatment compositions and oil-based ink compositions.

Copending Application U.S. Ser. No. 11/290,207, filed concurrently herewith, entitled "Photoinitiator With Phase Change Properties and Gellant Affinity," with the named inventors Peter G. Odell, Eniko Toma, and Jennifer L. Belelie, the disclosure of which is totally incorporated herein by reference, discloses a compound of the formula

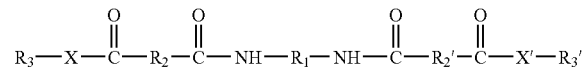

wherein $R_1$ is an alkylene, arylene, arylalkylene, or alkylarylene group, $R_2$ and $R_2'$ each, independently of the other, are alkylene, arylene, arylalkylene, or alkylarylene groups, $R_3$ and $R_3'$ each, independently of the other, are either (a) photoinitiating groups, or (b) groups which are alkyl, aryl, arylalkyl, or alkylaryl groups, provided that at least one of $R_3$ and $R_3'$ is a photoinitiating group, and X and X' each, independently of the other, is an oxygen atom or a group of the formula —$NR_4$—, wherein $R_4$ is a hydrogen atom, an alkyl group, an aryl group, an arylalkyl group, or an alkylaryl group.

Copending Application U.S. Ser. No. 11/290,202, filed concurrently herewith, entitled "Phase Change Inks Containing Photoinitiator With Phase Change Properties and Gellant Affinity," with the named inventors Peter G. Odell, Eniko Toma, and Jennifer L. Belelie, the disclosure of which is totally incorporated herein by reference, discloses a phase change ink comprising a colorant and an ink vehicle, said ink vehicle comprising (a) at least one radically curable monomer compound, and (b) a compound of the formula

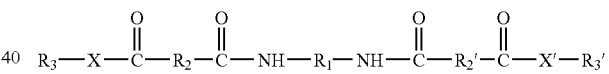

wherein $R_1$ is an alkylene, arylene, arylalkylene, or alkylarylene group, $R_2$ and $R_2'$ each, independently of the other, are alkylene, arylene, arylalkylene, or alkylarylene groups, $R_3$ and $R_3'$ each, independently of the other, are either (a) photoinitiating groups, or (b) groups which are alkyl, aryl, arylalkyl, or alkylaryl groups, provided that at least one of $R_3$ and $R_3'$ is a photoinitiating group, and X and X' each, independently of the other, is an oxygen atom or a group of the formula —$NR_4$—, wherein $R_4$ is a hydrogen atom, an alkyl group, an aryl group, an arylalkyl group, or an alkylaryl group.

Copending Application U.S. Ser. No. 11/290,122, filed concurrently herewith, entitled "Curable Amide Gellant Compounds," with the named inventors Eniko Toma, Peter G. Odell, Adela Goredema, and Jennifer L. Belelie, the disclosure of which is totally incorporated herein by reference, discloses a compound of the formula

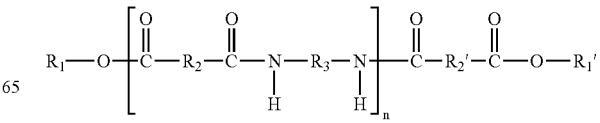

wherein $R_1$ and $R_1'$ each, independently of the other, is an alkyl group having at least one ethylenic unsaturation, an arylalkyl group having at least one ethylenic unsaturation, or an alkylaryl group having at least one ethylenic unsaturation, $R_2$, $R_2'$, and $R_3$ each, independently of the others, are alkylene groups, arylene groups, arylalkylene groups, or alkylarylene groups, and n is an integer representing the number of repeat amide units and is at least 1.

Copending Application U.S. Ser. No. 11/290,121, filed concurrently herewith, entitled "Phase Change Inks Containing Curable Amide Gellant Compounds," with the named inventors Eniko Toma, Jennifer L. Belelie, and Peter G. Odell, the disclosure of which is totally incorporated herein by reference, discloses a phase change ink comprising a colorant, an initiator, and a phase change ink carrier, said carrier comprising at least one radically curable monomer compound and a compound of the formula

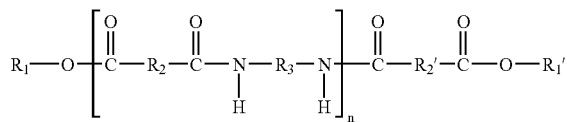

wherein $R_1$ and $R_1'$ each, independently of the other, is an alkyl group having at least one ethylenic unsaturation, an arylalkyl group having at least one ethylenic unsaturation, or an alkylaryl group having at least one ethylenic unsaturation, $R_2$, $R_2'$, and $R_3$ each, independently of the others, are alkylene groups, arylene groups, arylalkylene groups, or alkylarylene groups, and n is an integer representing the number of repeat amide units and is at least 1. Also disclosed is a method of printing with the phase change ink.

Copending Application U.S. Ser. No. 11/289,882, filed concurrently herewith, entitled "Process for Making Curable Amide Gellant Compounds," with the named inventors Eniko Toma, Adela Goredema, Jennifer L. Belelie, and Peter G. Odell, the disclosure of which is totally incorporated herein by reference, discloses a process for preparing a compound of the formula

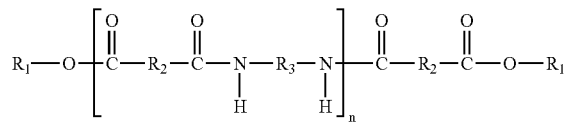

wherein $R_1$ is an alkyl group having at least one ethylenic unsaturation, an arylalkyl group having at least one ethylenic unsaturation, or an alkylaryl group having at least one ethylenic unsaturation, $R_2$ and $R_3$ each, independently of the others, are alkylene groups, arylene groups, arylalkylene groups, or alkylarylene groups, and n is an integer representing the number of repeat amide units and is at least 1, said process comprising: (a) reacting a diacid of the formula

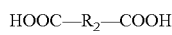

with a diamine of the formula

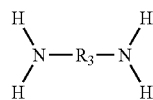

in the presence of a catalyst, a solvent and a coupling agent to form an oligoamide intermediate;

and (b) reading the oligoamide intermediate with an alcohol of the formula

to form the product.

BACKGROUND

Disclosed herein are curable ester-terminated oligoamide compounds and methods for preparing them. One embodiment disclosed herein is directed to a process for preparing a compound of the formula

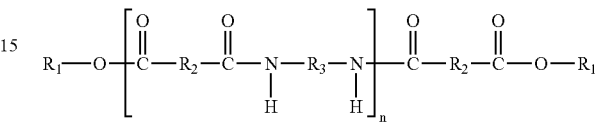

wherein $R_1$ is (i) an alkyl group having at least one ethylenic unsaturation therein (including linear and branched, cyclic and acyclic, and substituted and unsubstituted alkyl groups, and wherein hetero atoms either may or may not be present in the alkyl group), (ii) an arylalkyl group having at least one ethylenic unsaturation therein (including substituted and unsubstituted arylalkyl groups, wherein the alkyl portion of the arylalkyl group can be linear or branched, cyclic or acyclic, and substituted or unsubstituted, and wherein hetero atoms either may or may not be present in either the aryl or the alkyl portion of the arylalkyl group), or (iii) an alkylaryl group having at least one ethylene unsaturation therein (including substituted and unsubstituted alkylaryl groups, wherein the alkyl portion of the alkylaryl group can be linear or branched, cyclic or acyclic, and substituted or unsubstituted, and wherein hetero atoms either may or may not be present in either the aryl or the alkyl portion of the alkylaryl group), $R_2$ and $R_3$ each, independently of the others, are (i) alkylene groups, including linear and branched, saturated and unsaturated, cyclic and acyclic, and substituted and unsubstituted alkylene groups, and wherein hetero atoms either may or may not be present in the alkylene group, (ii) arylene groups, including substituted and unsubstituted arylene groups, and wherein hetero atoms either may or may not be present in the arylene group, (iii) arylalkylene groups, including substituted and unsubstituted arylalkylene groups, wherein the alkyl portion of the arylalkylene group can be linear or branched, saturated or unsaturated, cyclic or acyclic, and substituted or unsubstituted, and wherein hetero atoms either may or may not be present in either the aryl or the alkyl portion of the arylalkylene group, or (iv) alkylarylene groups, including substituted and unsubstituted alkylarylene groups, wherein the alkyl portion of the alkylarylene group can be linear or branched, saturated or unsaturated, cyclic or acyclic, and substituted or unsubstituted, and wherein hetero atoms either may or may not be present in either the aryl or the alkyl portion of the alkylarylene group, and n is an integer representing the number of repeat amide units and is at least 1, said process comprising: (a) reacting a diacid of the formula

with a diamine of the formula

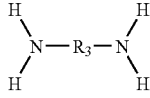

in the absence of a solvent while removing water from the reaction mixture to form an acid-terminated oligoamide intermediate of the formula

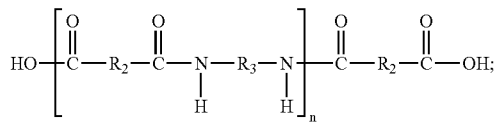

and (b) reacting the acid-terminated oligoamide intermediate with a monoalcohol of the formula

in the presence of a coupling agent and a catalyst to form the product of the formula

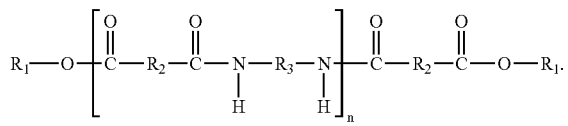

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications DE 4205636AL and DE 4205713AL, the disclosures of each of which are totally incorporated herein by reference.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 4,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking, industrial marking, and labelling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. No. 3,653,932, U.S. Pat. No. 4,390,369, U.S. Pat. No. 4,484,948, U.S. Pat. No. 4,684,956, U.S. Pat. No. 4,851,045, U.S. Pat. No. 4,889,560, U.S. Pat. No. 5,006,170, U.S. Pat. No. 5,151,120, U.S. Pat. No. 5,372,852, U.S. Pat. No. 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

U.S. Pat. No. 5,804,671 (Dones et al.), the disclosure of which is totally incorporated herein by reference, discloses a composition that is useful in the preparation of radiation curable coatings. The composition comprises the reaction product of an epoxy component comprising a diepoxide and an acid component comprising an ethylenically unsaturated carboxylic acid or reactive derivative thereof, reacted in the presence of a polyamide based on a polymerized fatty acid. The polyamide preferably has a number average molecular weight of less than about 10,000 g/mole. Also provided is a polymerizable composition comprising the reaction product and a reactive diluent. A method of coating a substrate is also provided which comprises applying to a substrate a composition comprising the reaction product and exposing said composition to radiation to cure said composition.

U.S. Pat. No. 5,889,076 (Dones et al.), the disclosure of which is totally incorporated herein by reference, discloses a composition that is useful in the preparation of radiation curable coatings. The composition comprises the reaction product of an epoxy component and an acid component comprising an ethylenically unsaturated carboxylic acid or reactive derivative thereof, reacted in the presence of, or post-reaction blended with, a polyamide based on a polymerized fatty acid. The polyamide preferably has a number average molecular weight of less than about 10,000 g/mole. Also provided is a polymerizable composition comprising the reaction product, the polyamide, and a reactive diluent. A method of coating a substrate is also provided which comprises applying to a substrate a composition comprising the reaction product and the polyamide and exposing said composition to radiation to cure said composition.

U.S. Pat. No. 6,239,189 (Narayan et al.), the disclosure of which is totally incorporated herein by reference, discloses a radiation-polymerizable composition containing at least one radiation curable acrylate resin oligomer prepared by reacting an alkoxylated polyol with a first acid component which includes an ethylenically unsaturated carboxylic acid, and a rheology modifier prepared by reacting a diepoxide with a second acid component which includes an ethylenically unsaturated carboxylic acid or reactive derivative thereof in the presence of a polyamide based on a polymerized fatty acid. The ethylenically unsaturated carboxylic acids of the first and second acid components are preferably acrylic acid or methacrylic acids. The diepoxide is preferably a diglycidyl ether such as bisphenol A. Colorants such as pigments or dyes optionally may be incorporated into the composition to form a printing ink which is curable by ultraviolet (UV) or electron beam radiation.

U.S. Pat. No. 6,316,517 (Dones et al.), the disclosure of which is totally incorporated herein by reference, discloses radiation-polymerizable compositions especially useful as or in a flush vehicle for making flushed pigments. The compositions contain at least one radiation-curable acrylated resin component and a copolymerizable rheology modifier component.

U.S. Patent Publication 2003/0036587 (Kozak), the disclosure of which is totally incorporated herein by reference, discloses rheology-controlled epoxy-based compositions particularly well suited for use in coating applications such as in the assembly of ink jet printheads for the printing industry, and in the microelectronics industry such as in the assembly of semiconductor devices.

U.S. Pat. No. 6,586,492 (Caiger et al.), the disclosure of which is totally incorporated herein by reference, discloses an ink jet ink including an ink jet vehicle and a colorant. The vehicle includes at least 35 percent by weight radiation curable material based on the total vehicle weight. The vehicle may but does not necessarily include a thickener. The vehicle is a paste or a solid at 20° C. and has a viscosity of less than 25 centipoise between 40° C. and 130° C.

U.S. Pat. No. 6,467,897 (Wu et al.), the disclosure of which is totally incorporated herein by reference, discloses compositions that incorporate surface modified, nanometer sized, inorganic oxide particles into energy curable fluids. The surface modification aspect allows the compatibility between the particles and fluid to be controllably adjusted to achieve a wide range of rheological characteristics. For printing, preferred compositions have favorable dot gain and thickness build up. When the composition is cured, the presence of the particles also helps improve physical properties such as hardness, modulus, abrasion resistance, refractive index, and the like. The compositions are particularly well-suited for forming printed, radiation cured features on substrates such as paper, signs, walkways, roadways, motor vehicles, boats, aircraft, furniture, equipment, and the like.

U.S. Pat. No. 6,896,937 (Woudenberg), the disclosure of which is totally incorporated herein by reference, discloses radiation-curable ink compositions and methods of printing including the compositions. In some embodiments, a radiation-curable hot melt ink composition includes a colorant, a polymerizable monomer, and a photoinitiating system. The photoinitiating system can include 0.5 to 1.5 percent by weight of an aromatic ketone photoinitiator, 2 to 10 percent by weight of an amine synergist, 3 to 8 percent by weight of an alpha-cleavage type photoinitiator, and 0.5 to 1.5 percent by weight of a photosensitizer.

While known compositions and processes are suitable for their intended purposes, a need remains for improved phase change ink compositions. In addition, a need remains for phase change inks that produce images with improved scratch resistance. Further, a need remains for phase change inks that produce images with improved adhesion to substrates such as paper. Additionally, a need remains for ultraviolet curable compounds that are soluble in phase change ink carriers. There is also a need for ultraviolet curable compounds that can be incorporated into phase change ink carriers without adversely affecting the viscosity characteristics of the ink at desired jetting temperatures. In addition, there is a need for ultraviolet curable compounds that can be incorporated into phase change ink carriers without adversely affecting the melting point of the ink. Further, there is a need for ultraviolet curable phase change inks that can be used in ink jet printing processes wherein the ink is first jetted onto an intermediate transfer member and subsequently transferred from the transfer member to a final substrate such as paper or transparency material. Additionally, there is a need for ultraviolet curable phase change inks that can be used in ink jet printing processes wherein the ink is jetted directly onto a final substrate such as paper or transparency material. A need also remains for phase change inks that generate images that exhibit improved robustness on the final recording sheet. In addition, a need remains for phase change inks that generate images with improved toughness. Further, a need remains for phase change inks that can be jetted at reduced temperatures. Additionally, a need remains for phase change inks that enable control of dot spread of the ink, particularly in processes wherein the ink is jetted directly onto a final substrate. There is also a need for phase change inks that enable production of images that exhibit improved archival color properties. In addition, there is a need for phase change inks wherein the ink does not bleed excessively into the substrate, particularly in processes wherein the ink is jetted directly onto a final substrate. Further, there is a need for phase change inks wherein the ink does not generate an undesirably high pile height and wherein an unnecessarily high number of drops are needed to create the image, particularly in processes wherein the ink is jetted directly onto a final substrate. Additionally, there is a need for phase change inks wherein the ink generates images with reduced showthrough. A need also remains for phase change inks wherein the increased viscosity of the ink during photoinitiation reduces the rate of diffusion of oxygen and its inhibitory effect in the ink, thereby increasing the efficiency of cure.

SUMMARY

Disclosed herein is a process for preparing a compound of the formula

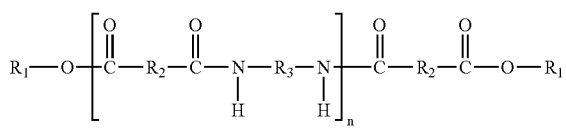

wherein $R_1$ is (i) an alkyl group having at least one ethylenic unsaturation therein (including linear and branched, cyclic and acyclic, and substituted and unsubstituted alkyl groups, and wherein hetero atoms either may or may not be present in the alkyl group), (ii) an arylalkyl group having at least one ethylenic unsaturation therein (including substituted and unsubstituted arylalkyl groups, wherein the alkyl portion of the arylalkyl group can be linear or branched, cyclic or acyclic, and substituted or unsubstituted, and wherein hetero atoms either may or may not be present in either the aryl or the alkyl portion of the arylalkyl group), or (iii) an alkylaryl group having at least one ethylenic unsaturation therein (including substituted and unsubstituted alkylaryl groups, wherein the alkyl portion of the alkylaryl group can be linear or branched, cyclic or acyclic, and substituted or unsubstituted, and wherein hetero atoms either may or may not be present in either the aryl or the alkyl portion of the alkylaryl group), $R_2$ and $R_3$ each, independently of the others, are (i) alkylene groups, including linear and branched, saturated and unsaturated, cyclic and acyclic, and substituted and unsubstituted alkylene groups, and wherein hetero atoms either may or may not be present in the alkylene group, (ii) arylene groups, including substituted and unsubstituted arylene groups, and wherein hetero atoms either may or may not be present in the arylene group, (iii) arylalkylene groups, including substituted and unsubstituted arylalkylene groups, wherein the alkyl portion of the arylalkylene group can be linear or branched, saturated or unsaturated, cyclic or acyclic, and substituted or unsubstituted, and wherein hetero atoms either may or may not be present in either the aryl or the alkyl portion of the arylalkylene group, or (iv) alkylarylene groups, including substituted and unsubstituted alkylarylene groups, wherein the alkyl portion of the alkylarylene group can be linear or branched, saturated or unsaturated, cyclic or acyclic, and substituted or unsubstituted, and wherein hetero atoms either may or may not be present in either the aryl or the alkyl portion of the alkylarylene group, and n is an integer representing the number of repeat amide units and is at least 1, said process comprising: (a) reacting a diacid of the formula

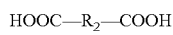
HOOC—$R_2$—COOH with a diamine of the formula

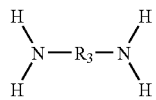

in the absence of a solvent while removing water from the reaction mixture to form an acid-terminated oligoamide intermediate of the formula

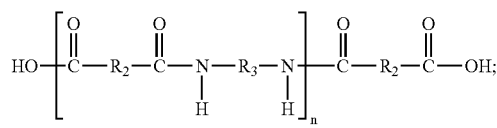

and (b) reacting the acid-terminated oligoamide intermediate with a monoalcohol of the formula

$R_1$—OH in the presence of a coupling agent and a catalyst to form the product of the formula

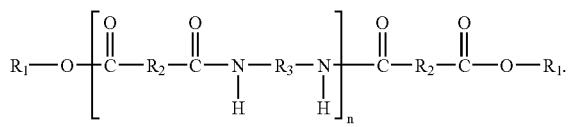

DETAILED DESCRIPTION

The compounds disclosed herein are of the formula

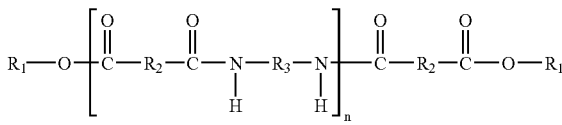

wherein:

$R_1$ is:

(i) an alkyl group having at least one ethylenic unsaturation therein (including linear and branched, cyclic and acyclic, and substituted and unsubstituted alkyl groups, and wherein hetero atoms, such as oxygen, nitrogen, sulfur, silicon, phosphorus, boron, and the like either may or may not be present in the alkyl group), in one embodiment with at least about 2 carbon atoms, in another embodiment with at least about 3 carbon atoms, and in yet another embodiment with at least about 4 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, (ii) an arylalkyl group having at least one ethylenic unsaturation therein (including substituted and unsubstituted arylalkyl groups, wherein the alkyl portion of the arylalkyl group can be linear or branched, cyclic or acyclic, and substituted or unsubstituted, and wherein hetero atoms, such as oxygen, nitrogen, sulfur, silicon, phosphorus, boron, and the like either may or may not be present in either the aryl or the alkyl portion of the arylalkyl group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, such as benzyl or the like, or (iii) an alkylaryl group having at least one ethylenic unsaturation therein (including substituted and unsubstituted alkylaryl groups, wherein the alkyl portion of the alkylaryl group can be linear or branched, cyclic or acyclic, and substituted or unsubstituted, and wherein hetero atoms, such as oxygen, nitrogen, sulfur, silicon, phosphorus, boron, and the like either may or may not be present in either the aryl or the alkyl portion of the alkylaryl group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, such as tolyl or the like, wherein the substituents on the substituted alkyl, arylalkyl, and alkylaryl groups can be (but are not limited to) halogen atoms, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring;

$R_2$ is:

(i) an alkylene group (wherein an alkylene group is defined as a divalent aliphatic group or alkyl group, including linear and branched, saturated and unsaturated, cyclic and acyclic, and substituted and unsubstituted alkylene groups, and wherein hetero atoms, such as oxygen, nitrogen, sulfur, silicon, phosphorus, boron, and the like either may or may not be present in the alkylene group), in one embodiment with at least 2 carbon atoms, in another embodiment with at least about 4 carbon atoms, in yet another embodiment with at least about 6 carbon atoms, in still another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, and in yet another embodiment with at least about 36 carbon atoms, and in one embodiment with no more than about 100 carbon atoms, in another embodiment with no more than about 60 carbon atoms, and in yet another embodiment with no more than about 50 carbon atoms, although the number of carbon atoms can be outside of these ranges, (ii) an arylene group (wherein an arylene group is defined as a divalent aromatic group or aryl group, including substituted and unsubstituted arylene groups, and wherein hetero atoms, such as oxygen, nitrogen, sulfur, silicon, phosphorus, boron, and the like either may or may not be present in the arylene group), in one embodiment with at least about 5 carbon atoms, and in another embodiment with at least about 6 carbon atoms, and in one embodiment with no more than about 100 carbon atoms, in another embodiment with no more than about 60 carbon atoms, and in yet another embodiment with no more than about 50 carbon atoms, although the number of carbon atoms can be outside of these ranges, (iii) an arylalkylene group (wherein an arylalkylene group is defined as a divalent arylalkyl group, including substituted and unsubstituted arylalkylene groups, wherein the alkyl portion of the arylalkylene group can be linear or branched, saturated or unsaturated, cyclic or acyclic, and substituted or unsubstituted, and wherein hetero atoms, such as oxygen, nitrogen, sulfur, silicon, phosphorus, boron, and the like either may or may not be present in either the aryl or the alkyl portion of the arylalkylene group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 50 carbon atoms, although the number of carbon atoms can be outside of these ranges, or (iv) an alkylarylene group (wherein an alkylarylene group is defined as a divalent alkylaryl group, including substituted and unsubstituted alkylarylene groups, wherein the alkyl portion of the alkylarylene group can be linear or branched, saturated or unsaturated, cyclic or acyclic, and substituted or unsubstituted, and wherein hetero atoms, such as oxygen, nitrogen, sulfur, silicon, phosphorus, boron, and the like either may or may not be present in either the aryl or the alkyl portion of the alkylarylene group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 50 carbon atoms, although the number of carbon atoms can be outside of these ranges, wherein the substituents on the substituted alkylene, arylene, arylalkylene, and alkylarylene groups can be (but are not limited to) pyridine groups, pyridinium groups, ether groups, aldehyde groups, ketone groups, ester groups, amide groups, carbonyl groups, thiocarbonyl groups, sulfide groups, phosphine groups, phosphonium groups, phosphate groups, nitrile groups, mercapto groups, nitro groups, nitroso groups, acyl groups, acid anhydride groups, azide groups, azo groups, thiocyanato groups, carboxylate groups, urethane groups, urea groups, mixtures thereof, and the like, wherein two or more substituents can be joined together to form a ring;

$R_3$ is:

(i) an alkylene group (wherein an alkylene group is defined as a divalent aliphatic group or alkyl group, including linear and branched, saturated and unsaturated, cyclic and acyclic, and substituted and unsubstituted alkylene groups, and wherein hetero atoms, such as oxygen, nitrogen, sulfur, silicon, phosphorus, boron, and the like either may or may not be present in the alkylene group), in one embodiment with at least 2 carbon atoms, and in one embodiment with no more than about 80 carbon atoms, in another embodiment with no more than about 60 carbon atoms, in yet another embodiment with no more than about 50 carbon atoms, and in still another embodiment with no more than about 36 carbon atoms, although the number of carbon atoms can be outside of these ranges, (ii) an arylene group (wherein an arylene group is defined as a divalent aromatic group or aryl group, including substituted and unsubstituted arylene groups, and wherein hetero atoms, such as oxygen, nitrogen, sulfur, silicon, phosphorus, boron, and the like either may or may not be present in the arylene group), in one embodiment with at least about 5 carbon atoms, and in another embodiment with at least about 6 carbon atoms, and in one embodiment with no more than about 50 carbon atoms, in another embodiment with no more than about 25 carbon atoms, and in yet another embodiment with no more than about 18 carbon atoms, although the number of carbon atoms can be outside of these ranges, (iii) an arylalkylene group (wherein an arylalkylene group is defined as a divalent arylalkyl group, including substituted and unsubstituted arylalkylene groups, wherein the alkyl portion of the arylalkylene group can be linear or branched, saturated or unsaturated, cyclic or acyclic, and substituted or unsubstituted, and wherein hetero atoms, such as oxygen, nitrogen, sulfur, silicon, phosphorus, boron, and the like either may or may not be present in either the aryl or the alkyl portion of the arylalkylene group), in one embodiment with at least about 6 carbon atoms, and in another embodiment with at least about 7 carbon atoms, and in one embodiment with no more than about 50 carbon atoms, in another embodiment with no more than about 36 carbon atoms, and in yet another embodiment with no more than about 18 carbon atoms, although the number of carbon atoms can be outside of these ranges, or (iv) an alkylarylene group (wherein an alkylarylene group is defined as a divalent alkylaryl group, including substituted and unsubstituted alkylarylene groups, wherein the alkyl portion of the alkylarylene group can be linear or branched, saturated or unsaturated, cyclic or acyclic, and substituted or unsubstituted, and wherein hetero atoms, such as oxygen, nitrogen, sulfur, silicon, phosphorus, boron, and the like either may or may not be present in either the aryl or the alkyl portion of the alkylarylene group), in one embodiment with at least about 6 carbon atoms, and in another embodiment with at least about 7 carbon atoms, and in one embodiment with no more than about 50 carbon atoms, in another embodiment with no more than about 36 carbon atoms, and in yet another embodiment with no more than about 18 carbon atoms, although the number of carbon atoms can be outside of these ranges, wherein the substituents on the substituted alkylene, arylene, arylalkylene, and alkylarylene groups can be (but are not limited to) pyridine groups, pyridinium groups, ether groups, aldehyde groups, ketone groups, ester groups, amide groups, carbonyl groups, thiocarbonyl groups, sulfide groups, phosphine groups, phosphonium groups, phosphate groups, nitrile groups, mercapto groups, nitro groups, nitroso groups, acyl groups, acid anhydride groups, azide groups, azo groups, carboxylate groups, urethane groups, urea groups, mixtures thereof, and the like, wherein two or more substituents can be joined together to form a ring;

and n is an integer representing the number of repeat amide units, being in one embodiment at least 1, and in one embodiment no more than about 20, in another embodiment no more than about 15, and in yet another embodiment no more than about 10, although the value of n can be outside of these ranges.

In one specific embodiment, $R_1$ is of the formula

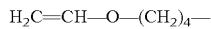
$H_2C=CH-O-(CH_2)_4-$

In another specific embodiment, $R_1$ is of the formula

$H_2C=CH-O-(CH_2)_2-O-(CH_2)_2-$

In yet another specific embodiment, $R_1$ is of the formula

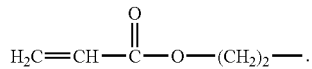

In still another specific embodiment, $R_1$ is of the formula

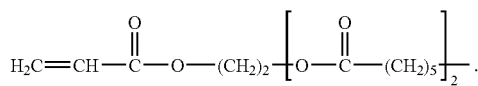

In another specific embodiment, $R_1$ is of the formula

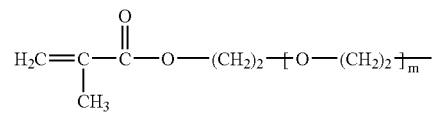

wherein m is an integer representing the number of repeating [O—(CH$_2$)$_2$] units, and is in one specific embodiment 2 and is in another specific embodiment 5.

In yet another specific embodiment, $R_1$ is of the formula

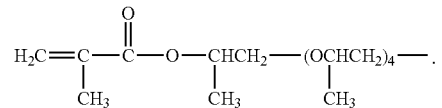

In one specific embodiment, $R_2$ is a group of the formula —$C_{34}H_{56+a}$— and is a branched alkylene group which may include unsaturations and cyclic groups, wherein a is an integer of 0, 1, 2, 3, 4, 5, 6, 7, 8, 9, 10, 11, or 12, including (but not limited to) isomers of the formula

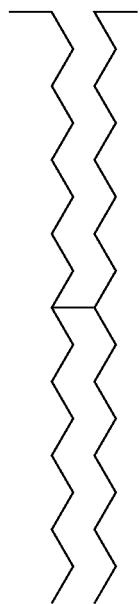

In one specific embodiment, $R_3$ is an ethylene (—CH$_2$CH$_2$—) group.

In one specific embodiment, n is 1 or 2.

In one specific embodiment, the compound is of the formula

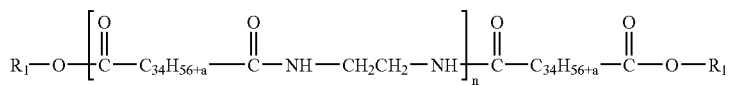

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

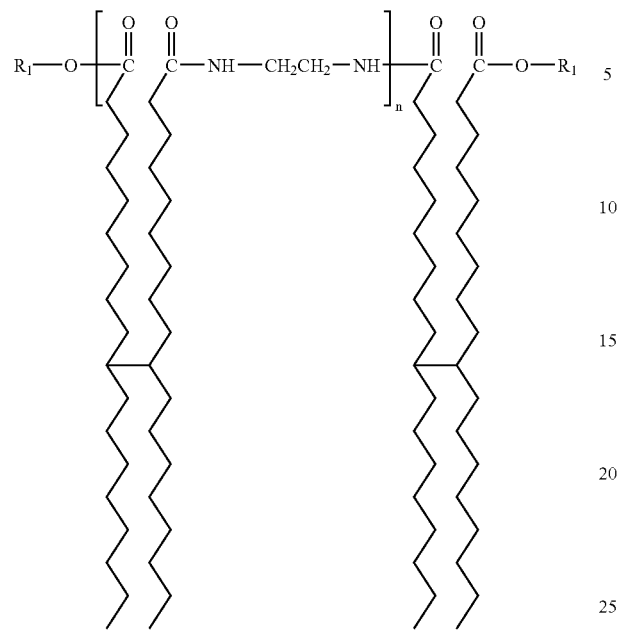
wherein n is 1 or 2,
Additional specific examples of compounds of this formula include those of the formula
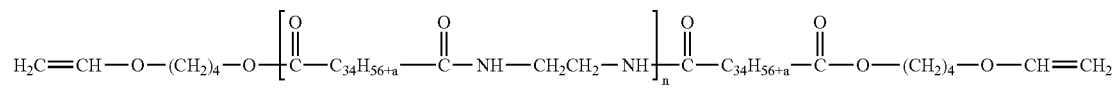
wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12 including (but not limited to) isomers of the formula
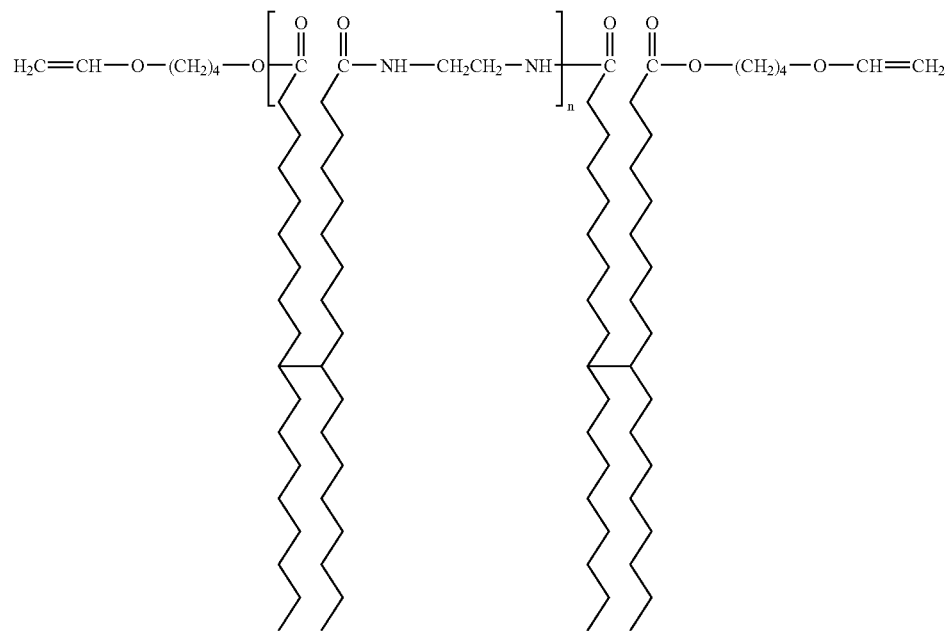

wherein n is 1 or 2, those of the formula

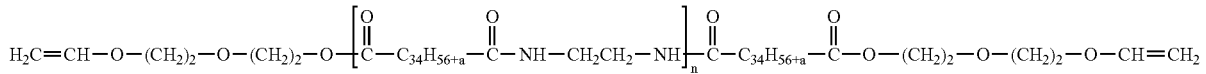

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

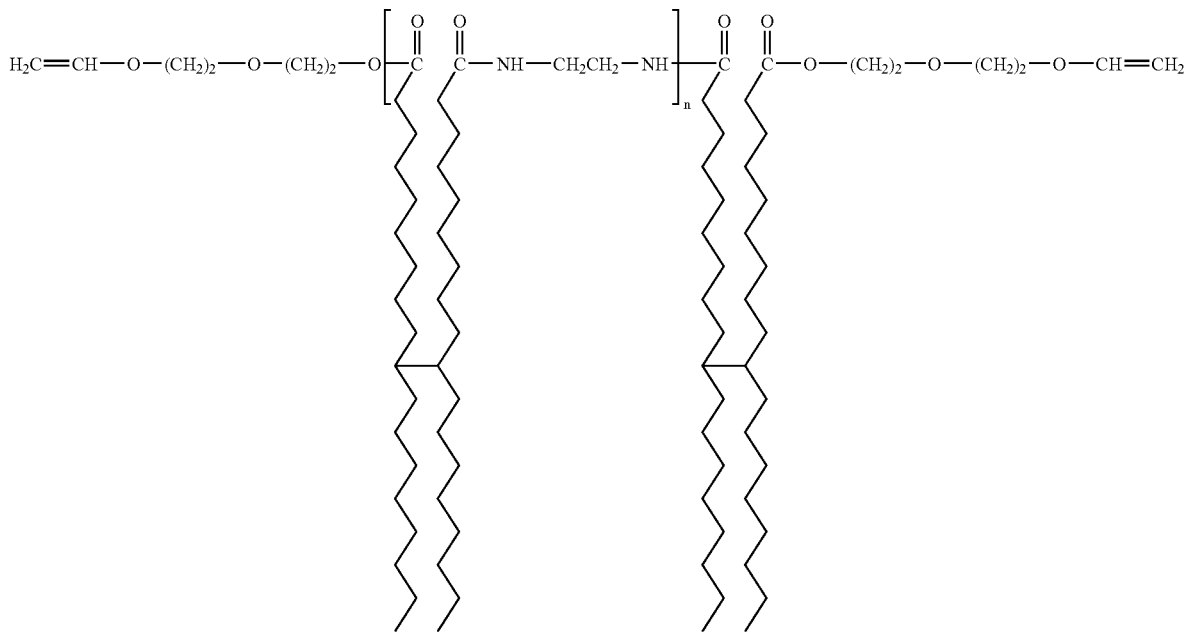

wherein n is 1 or 2, those of the formula

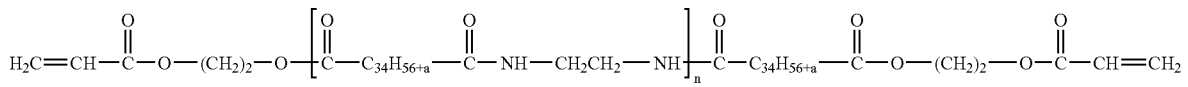

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

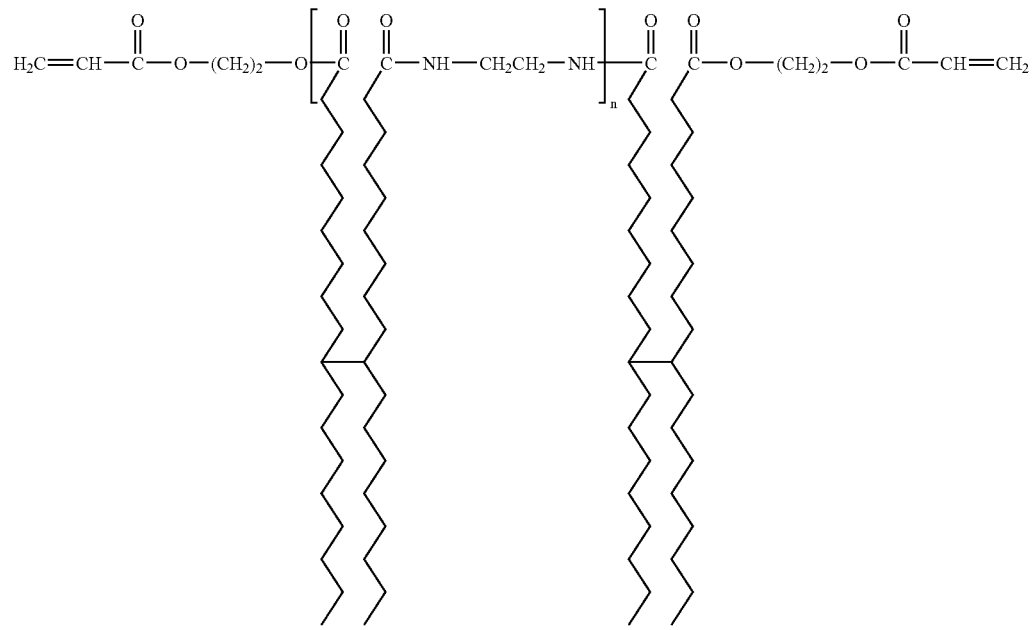
wherein n is 1 or 2, those of the formula
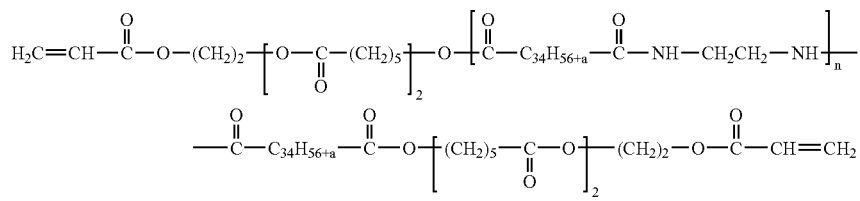
wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula
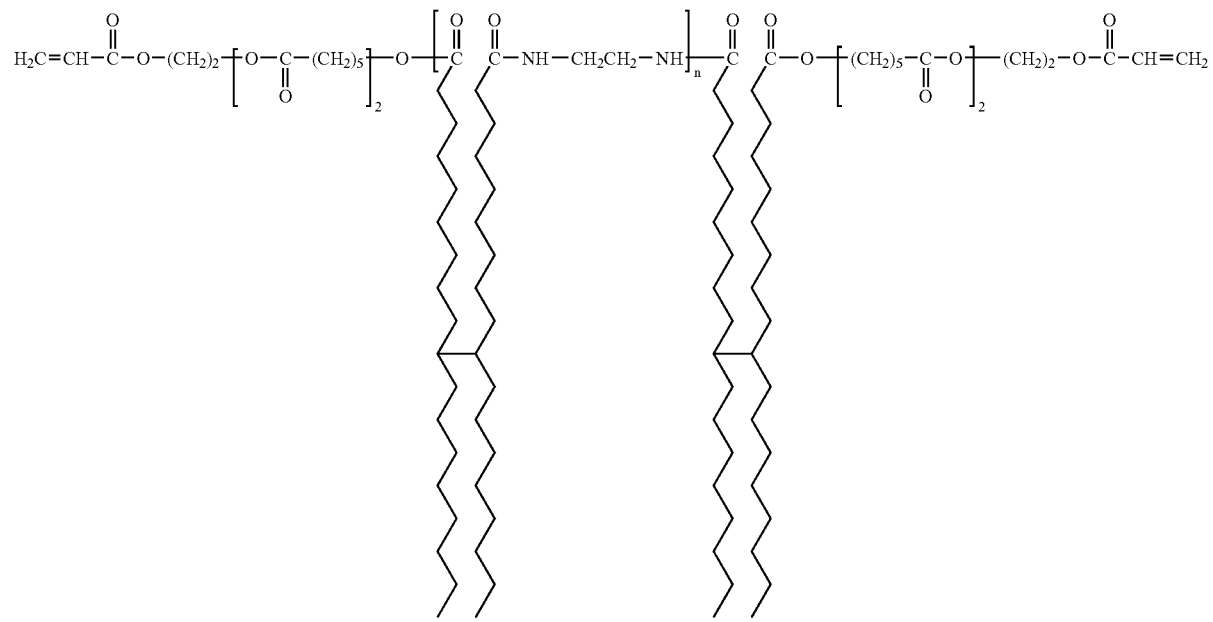

wherein n is 1 or 2, those of the formula

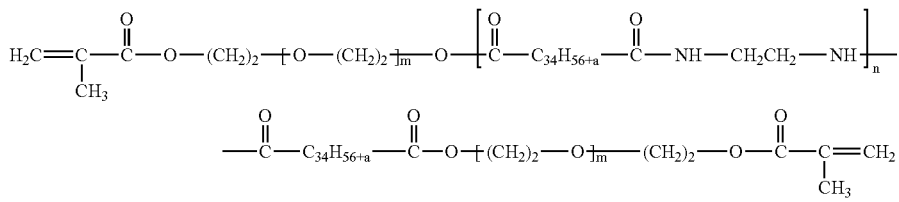

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, wherein m is an integer representing the number of repeating [O—(CH$_2$)$_2$] units, and is in one specific embodiment 2 and is in another specific embodiment 5, including (but not limited to) isomers of the formula

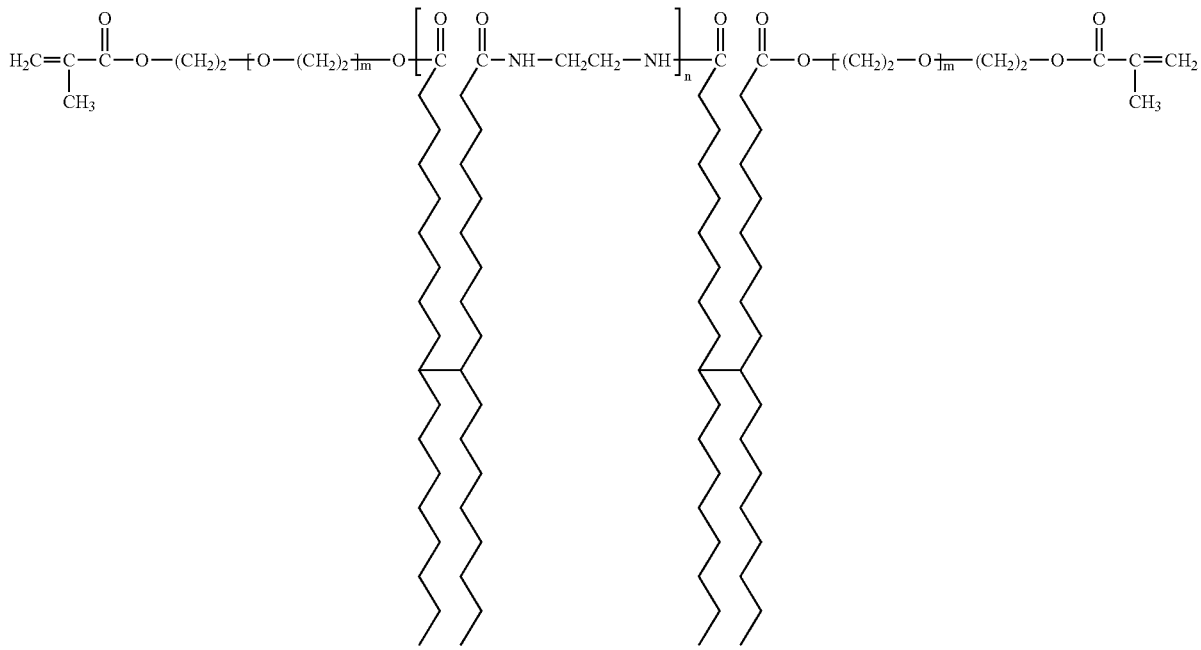

wherein n is 1 or 2, wherein m is an integer representing the number of repeating [O—(CH$_2$)$_2$] units, and is in one specific embodiment 2 and is in another specific embodiment 5, those of the formula

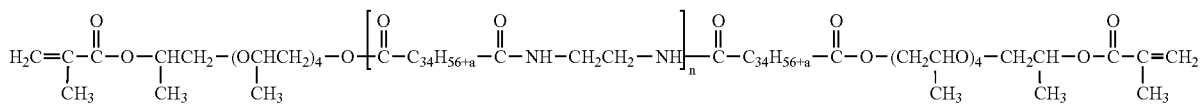

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

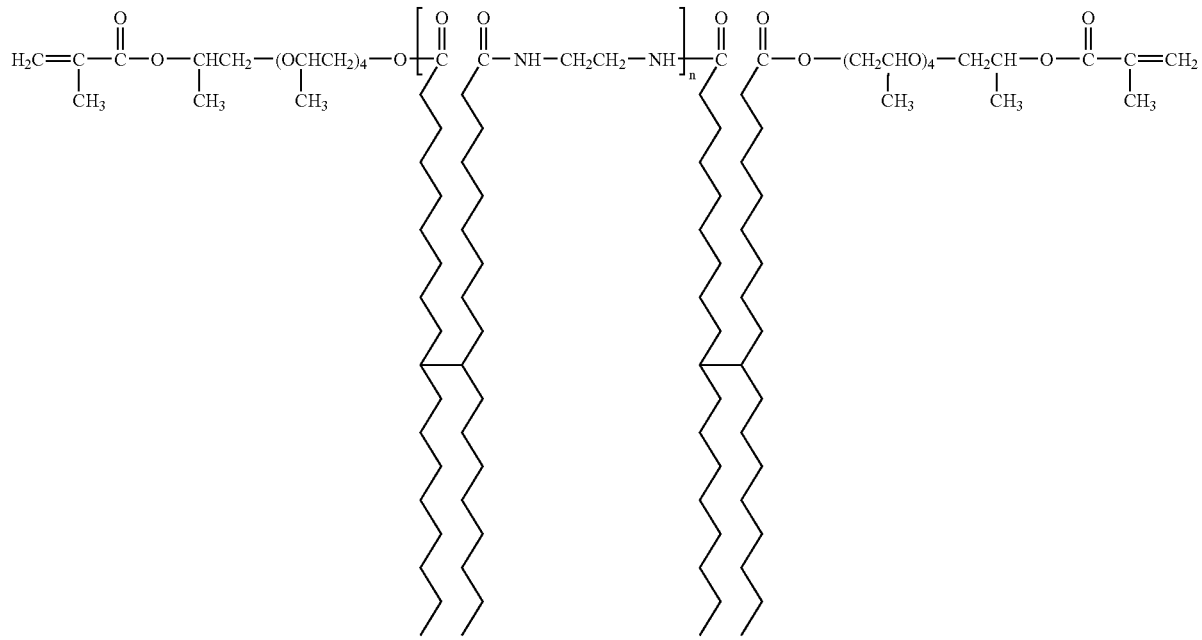

wherein n is 1 or 2, and the like, as well as mixtures thereof.

Compounds as disclosed herein can be prepared by as disclosed herein. For example, in one specific embodiment, the compounds can be prepared by first reacting about n+1 molar equivalents of a diacid of the formula

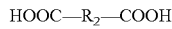

and about n molar equivalent of a diamine of the formula

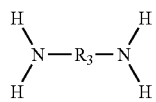

under neat conditions (i.e., in the absence of a solvent) at elevated temperatures while removing water from the reaction mixture to form an acid-terminated oligoamide of the formula

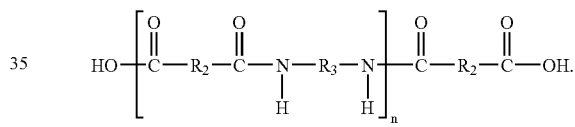

Thereafter, the acid-terminated oligoamide thus formed is reacted with about 2 molar equivalents of a monoalcohol of the formula

by use of a coupling agent such as 1,3-dicyclohexylcarbodiimide (DCC) in the presence of a catalyst such as 4-dimethylaminopyridine (DMAP) in the presence of a solvent such as methylene chloride (CH$_2$Cl$_2$) at reduced temperatures. The reaction proceeds as follows:

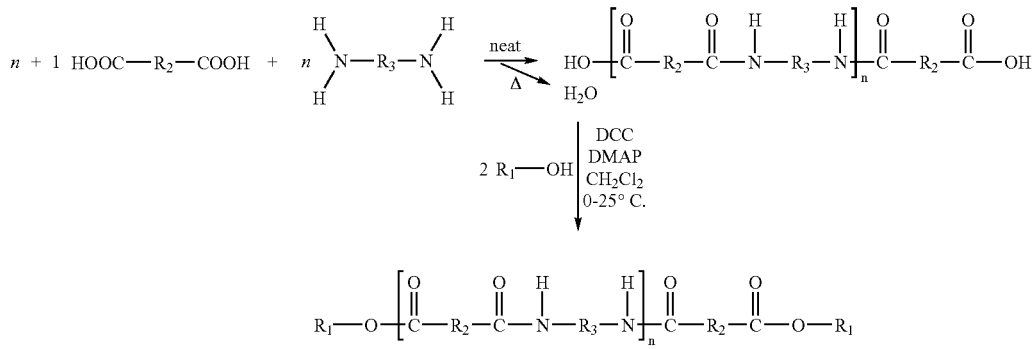

For example, when n=1, the diacid and the diamine are present in any desired or effective relative amounts, in one embodiment at least about 0.75 mole of diamine per every 2 moles of diacid, in another embodiment at least about 0.85 mole of diamine per every 2 moles of diacid, and in yet another embodiment at least about 1 mole of diamine per every 2 moles of diacid, and in one embodiment no more than about 1.5 moles of diamine per every 2 moles of diacid, in another embodiment no more than about 1.35 moles of diamine per every 2 moles of diacid, and in yet another embodiment no more than about 1.25 moles of diamine per every 2 moles of diacid, although the relative amounts can be outside of these ranges.

Water can be removed from the reaction mixture between the diacid and the diamine by any desired or effective method, such as by a Dean-Stark trap, molecular sieves or other drying agents, or the like.

The reaction between the diacid and the diamine generally is run neat, i.e., in the absence of a solvent.

The reaction between the diacid and the diamine can be carried out at any desired or effective temperature, in one embodiment at least about 130° C., in another embodiment at least about 140° C., and in yet another embodiment at least about 155° C., and one embodiment no more than about 180° C., in another embodiment no more than about 175° C., and in yet another embodiment no more than about 165° C., although the temperature can be outside of these ranges.

The reaction between the diacid and the diamine can be carried out for any desired or effective period of time, in one embodiment at least about 2 hours, in another embodiment at least about 2.5 hours, and in yet another embodiment at least about 3 hours, and in one embodiment no more than about 5 hours, in another embodiment no more than about 4.5 hours, and in another embodiment no more than about 4 hours, although the period of time can be outside of these ranges.

Thereafter, the acid-terminated oligoamide intermediate and the monoalcohol are reacted in the presence of a coupling agent and a catalyst.

Examples of suitable coupling agents include 1,3-dicyclohexylcarbodiimide (DCC), of the formula

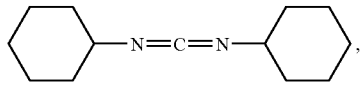

1-[3-(dimethylamino)propyl] 3-ethylcarbodiimide HCl (EDCl), N,N-carbonyldiimidazole, N-cyclohexyl-N'-(2-morpholinoethyl)-carbodiimide methyl-p-toluenesulfonate, (benzotriazol-1-yloxy)tris(dimethylamino)phosphonium hexafluorophosphate (BOP), (o-benzotriazol-1-yl)-N,N,N', N'-bis(tetramethylene)uronium hexafluorophosphate (HBTU), bis(2-oxo-3-oxazolidinyl)phosphonic chloride (BOP-Cl), (1H-1,2,3-benzotriazol-1-yloxy)tris(pyrrolidino) phosphonium hexafluorophosphate (PyBOP), and the like, as well as mixtures thereof.

Examples of suitable catalysts include 4-dimethylaminopyridine (DMAP), of the formula

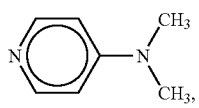

triethylamine, 1,8-diazabicyclo [5.4.0]undec-7-ene (DBU), and the like, as well as mixtures thereof.

The acid-terminated oligoamide intermediate and the monoalcohol are present in any desired or effective relative amounts, in one embodiment at least about 2 moles of monoalcohol per every 1 mole of acid-terminated oligoamide intermediate, in another embodiment at least about 2.15 moles of monoalcohol per every 1 mole of acid-terminated oligoamide intermediate, and in yet another embodiment at least about 2.25 moles of monoalcohol per every one mole of acid-terminated oligoamide intermediate, and in one embodiment no more than about 2.75 moles of monoalcohol per every 1 mole of acid-terminated oligoamide intermediate, in another embodiment no more than about 2.5 moles of monoalcohol per every 1 mole of acid-terminated oligoamide intermediate, and in yet another embodiment no more than about 2.4 moles of monoalcohol per every 1 mole of acid-terminated oligoamide intermediate, although the relative amounts can be outside of these ranges.

The acid-terminated oligoamide and the coupling agent are present in any desired or effective relative amounts, in one embodiment at least about 1.8 moles of coupling agent per every 1 mole of acid-terminated oligoamide, in another embodiment at least about 2 moles of coupling agent per every 1 mole of acid-terminated oligoamide, and in yet another embodiment at least about 2.2 moles of coupling agent per every one mole of acid-terminated oligoamide, and in one embodiment no more than about 3 moles of coupling agent per every 1 mole of acid-terminated oligoamide, in another embodiment no more than about 2.8 moles of coupling agent per every 1 mole of acid-terminated oligoamide, and in yet another embodiment no more than about 2.5 moles of coupling agent per every 1 mole of acid-terminated oligoamide, although the relative amounts can be outside of these ranges.

The catalyst and the acid-terminated oligoamide intermediate are present in any desired or effective relative amounts, in one embodiment at least about 0.05 mole of catalyst per every 1 mole of acid-terminated oligoamide intermediate, in another embodiment at least about 0.1 mole of catalyst per every 1 mole of acid-terminated oligoamide intermediate, and in yet another embodiment at least about 0.2 mole of catalyst per every one mole of acid-terminated oligoamide intermediate, and in one embodiment no more than about 1 mole of catalyst per every 1 mole of acid-terminated oligoamide intermediate, in another embodiment no more than about 0.8 mole of catalyst per every 1 mole of acid-terminated oligoamide intermediate, and in yet another embodiment no more than about 0.5 mole of catalyst per every 1 mole of acid-terminated oligoamide intermediate, although the relative amounts can be outside of these ranges.

Any desired or effective solvent can be employed. Examples of suitable solvents include methylene chloride, tetrahydrofuran, methyl ethyl ketone, toluene, dimethyl formamide, diethyl ether, hexane, ethyl acetate, and the like, as well as mixtures thereof.

The solvent can be present in any desired or effective amount, in one embodiment at least about 20 milliliters of solvent per gram of acid-terminated oligoamide intermediate, in another embodiment at least about 25 milliliters of solvent per gram of acid-terminated oligoamide intermediate, and in yet another embodiment at least about 30 milliliters of solvent per gram of acid-terminated oligoamide intermediate, and in one embodiment no more than about 100 milliliters of solvent per gram of acid-terminated oligoamide intermediate, in another embodiment no more than about 90 milliliters of solvent per gram of acid-terminated oligoamide intermediate, and in yet another embodiment no more than about 80 milliliters of solvent per gram of acid-terminated oligoamide intermediate, although the amount of solvent can be outside of these ranges.

The reaction between the acid-terminated oligoamide intermediate, the monoalcohol, and the coupling agent can be carried out at any desired or effective temperature, in one embodiment at least about 15° C., in another embodiment at least about 20° C., and in yet another embodiment at least about 25° C., and one embodiment no more than about 50° C., in another embodiment no more than about 40° C., and in yet another embodiment no more than about 35° C., although the temperature can be outside of these ranges.

The reaction between the acid-terminated oligoamide intermediate, the monoalcohol, and the coupling agent can be carried out for any desired or effective period of time, in one embodiment at least about 2 hours, in another embodiment at least about 2.5 hours, and in yet another embodiment at least about 3 hours, and in one embodiment no more than about 5 hours, in another embodiment no more than about 4.5 hours, and in another embodiment no more than about 4 hours, although the period of time can be outside of these ranges.

Subsequent to completion of the reaction, the product can be recovered by any desired or effective method, such as filtration of any solid by-products or washing the solution with water depending on the coupling agent used. The solvent can be removed by rotary evaporation. If needed, the product can be purified by washing with acetone and dried in a vacuum oven.

Many embodiments of the compounds thus prepared can exhibit gel-like behavior when present in solutions. Examples of materials in which they can be dissolved include curable monomers such as, for example, propoxylated neopentyl glycol diacrylate, such as SR9003, commercially available from Sartomer Co. Inc. By gel-like behavior is meant that they undergo a relatively sharp increase in viscosity over a relatively narrow temperature range. In one embodiment, some compounds as disclosed herein undergo a change in viscosity of at least about $10^3$ centipoise, in another embodiment at least about $10^5$ centipoise, and in yet another embodiment at least about $10^6$ centipoise over a temperature range of in one embodiment at least about 5° C., in another embodiment at least about 10° C., and in yet another embodiment at least about 30° C., although the viscosity change and temperature range can be outside of these ranges, and compounds that do not undergo changes within these ranges are also included herein.

At least some embodiments of the compounds disclosed herein can form a semi-solid gel at a first temperature. For example, when the compound is incorporated into a phase change ink, this temperature is below the specific temperature at which the ink is jetted. The semi-solid gel phase is a physical gel that exists as a dynamic equilibrium comprising one or more solid gellant molecules and a liquid solvent. The semi-solid gel phase is a dynamic networked assembly of molecular components held together by non-covalent interactions such as hydrogen bonding, Van der Waals interactions, aromatic non-bonding interactions, ionic or coordination bonding, London dispersion forces, or the like, which, upon stimulation by physical forces, such as temperature, mechanical agitation, or the like, or chemical forces, such as pH, ionic strength, or the like, can undergo reversible transitions from liquid to semi-solid state at the macroscopic level. The solutions containing the gellant molecules exhibit a thermally reversible transition between the semi-solid gel state and the liquid state when the temperature is varied above or below the gel point of the solution. This reversible cycle of transitioning between semi-solid gel phase and liquid phase can be repeated many times in the solution formulation.

The compounds disclosed herein are curable. "Curable" as used herein means polymerizable or chain extendable, i.e., a material that can be cured via polymerization, including (but not limited to) free radical polymerization or chain extension, cationic polymerization or chain extension, and/or in which polymerization is photoinitiated through use of a radiation sensitive photoinitiator. Radiation curable as used herein is intended to cover all forms of curing upon exposure to a radiation source, including (but not limited to) light and heat sources and including in the presence or absence of initiators. Examples of radiation curing include (but are not limited to) ultraviolet (UV) light, for example having a wavelength of from about 200 to about 400 nanometers, visible light, or the like, optionally in the presence of photoinitiators and/or sensitizers, e-beam radiation, optionally in the presence of photoinitiators, thermal curing, optionally in the presence of high temperature thermal initiators (and which are preferably largely inactive at the jetting temperature when used in phase change inks), and appropriate combinations thereof.

Specific embodiments will now be described in detail. These examples are intended to be illustrative, and the claims are not limited to the materials, conditions, or process parameters set forth in these embodiments. All parts and percentages are by weight unless otherwise indicated.

EXAMPLE I

A compound of the formula

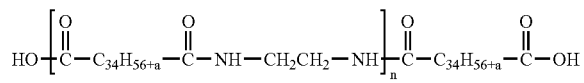

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12 and n is 1, including (but not limited to) isomers of the formula

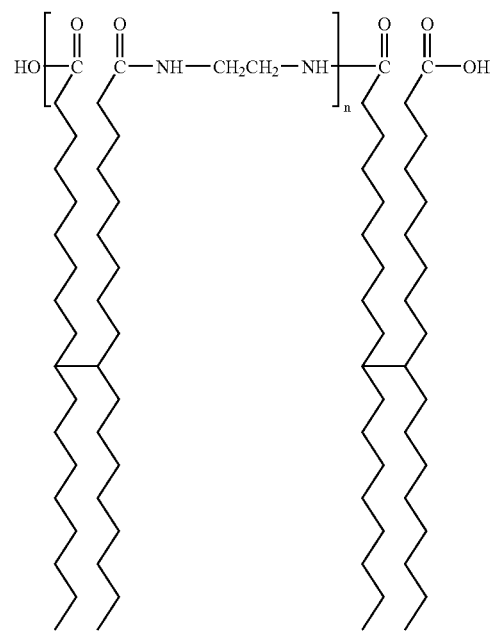

wherein n is 1 was prepared as follows. To a 3 neck, 250 mL round bottom flask equipped with a thermocouple, stir bar, stopper, Dean-Stark trap, reflux condenser, and argon inlet was added PRIPOL 1009 (C36 dimer acid mixture, including isomers of the formula

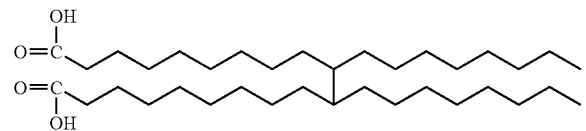

as well as other branched isomers which may include unsaturations and cyclic groups; 100 g, acid number 196 mgKOH/g, 95 wt %, obtained from Uniqema, New Castle, Del., (further information on C36 dimer acids of this type is disclosed in, for example, "Dimer Acids," *Kirk-Othmer Encyclopedia of Chemical Technology*, Vol. 8, 4$^{th}$ Ed. (1992), pp. 223 to 237), the disclosure of which is incorporated herein by reference) and IRGAFOS 168 (tris(2,4-di-(tert)-butylphenyl)phosphate), 0.20 g, 0.2 wt %, obtained from Ciba Specialty Chemicals, Basel, Switzerland). The system was purged with Ar for 15 minutes with one of the necks open, after which time the stopper was replaced. The temperature was set to 100° C. and the stirrer was set in motion. The stopper was quickly replaced with an addition funnel equipped with a septum and ethylene diamine (EDA, 5.25 g, 5.84 mL, 5 wt %, obtained from Sigma-Aldrich Chemical Company, Milwaukee, Wis.) was added to it via syringe. The EDA was added to the reaction mixture slowly dropwise, ensuring that the internal reaction temperature did not exceed 118° C. After the addition was complete, the temperature was raised slowly stepwise to 155° C., where it was kept until the water ceased collecting in the Dean-Stark trap (about 1.4 mL H$_2$O collected; reaction time was 2-3 h at 155° C.). The completion of the reaction was confirmed by $^1$H NMR analysis in CDCl$_3$: the triplet at δ2.34, corresponding to the protons alpha to the carboxylic acid groups, and the triplet at δ2.18, corresponding to the protons alpha to the carbonyl groups of the amides, were approximately in a 1:1 ratio. At the end of the reaction, the temperature was lowered to 130° C. and the clear, amber oil was poured from the flask into aluminum plates (recovered m=93 g). Acid number=101.1 mgKOH/g. $^1$H NMR (CDCl$_3$, 300 MHz) δ3.38 (4H, br. s), 2.53 (2H, br. s), 2.34 (4H, t, J=7.3 Hz), 2.18 (4H, t, J=7.6 Hz), 1.88-0.65 (138H, m).

EXAMPLE II

A compound of the formula

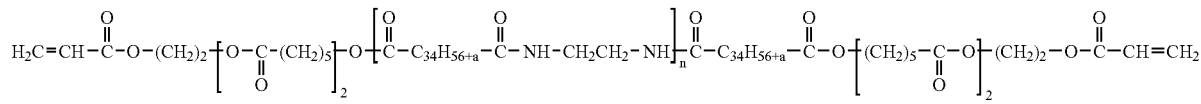

wherein —C$_{34}$H$_{56+a}$— represents a branched alkylene group which may include unsaturations and cyclic groups, wherein a is an integer of 0, 1, 2, 3, 4, 5, 6, 7, 8, 9, 10, 11, or 12 and n is 1, including (but not limited to) isomers of the formula

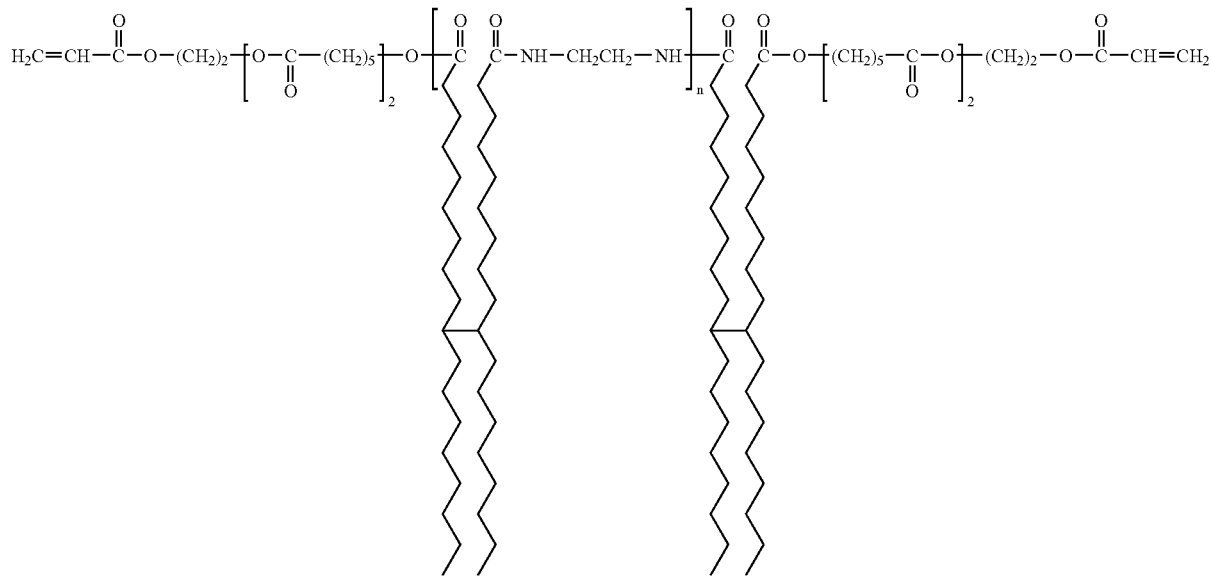

wherein n is 1 was prepared as follows. To a 3 neck, 2 L flask equipped with two dropping funnels, stir bar and argon inlet was added the oligoamide prepared as described in Example I (50 g, acid number 101.1, $n_{acid}$=9.01×10$^{-2}$ mol), 4-dimethylaminopyridine (1.10 g, 9.01×10$^{-3}$ mol, obtained from Sigma-Aldrich Chemical Company, Milwaukee, Wis.) and methylene chloride (1 L) and the reaction mixture was stirred until homogenous. N,N'-Dicyclohexylcarbodiimide (99 mL, 1 M solution in CH$_2$Cl$_2$, 9.90×10$^{-2}$ mol, obtained from Sigma-Aldrich Chemical Company) was added slowly dropwise and the reaction mixture was allowed to stir for 0.5 h before adding caprolactone acrylate (TONE M-100, 31.0 g, 9.01×10$^{-2}$ mol, obtained from Dow Chemical Company, Midland, Mich.). The reaction progress was followed via $^1$H NMR spectroscopy in CDCl$_3$: when the signal corresponding to the methylene protons alpha to the hydroxyl group (~δ3.6, t) were consumed, the reaction was complete. The reaction time was between 2-3 h. The reaction mixture was filtered to remove N,N'-dicyclohexylurea (byproduct) and the filtrate solvent was removed in vacuo. The residue was redissolved in a minimum amount of CH$_2$Cl$_2$, refiltered, and concentrated in vocuo. The residue was triturated with acetone and filtered to reveal an off-white solid (m=45 g). $^1$H NMR (CDCl$_3$, 300 MHz) δ6.38 (2H, d, J=15.8 Hz), 6.20 (2H, dd, J=15.8, 10.5 Hz), 5.89 (2H, d, J=10.5 Hz), 4.38-4.32 (8H, m), 4.09 (8H, t, J=6.6 Hz), 3.38 (4H, s), 2.53 (2H, br. s), 2.38-2.27 (12H, m), 2.18 (4H, t, J=7.6 Hz), 1.81-0.83 (162H, m).

EXAMPLE III

The process of Examples I and II is repeated except that the caprolactone acrylate is replaced with an equimolar amount of ethoxylated hydroxyethyl methacrylate CD570, available from Sartomer Company Inc. Exton, Pa.). It is believed that the product will be of the formula

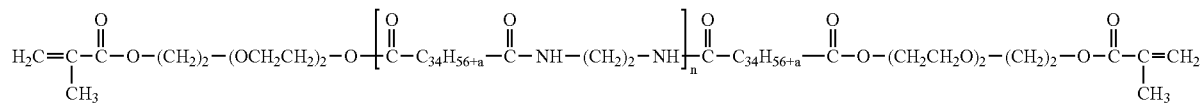

wherein —C$_{34}$H$_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

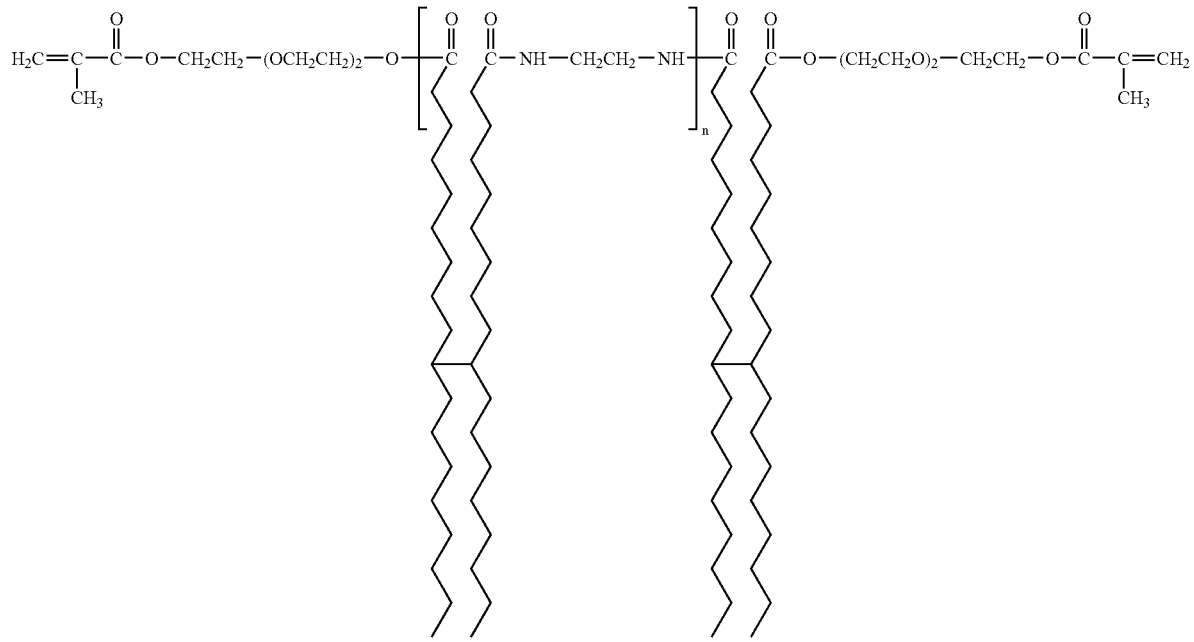

wherein n is 1.

EXAMPLE IV

The process of Examples I and II is repeated except that the caprolactone acrylate is replaced with an equimolar amount of polypropylene glycol monomethacrylate, available as SR604 from Sartomer Company Inc., Exton, Pa. It is believed that the product will be of the formula

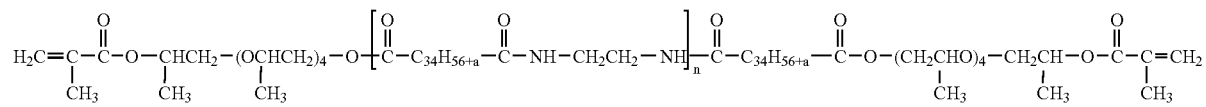

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12 and n is 1, including (but not limited to) isomers of the formula

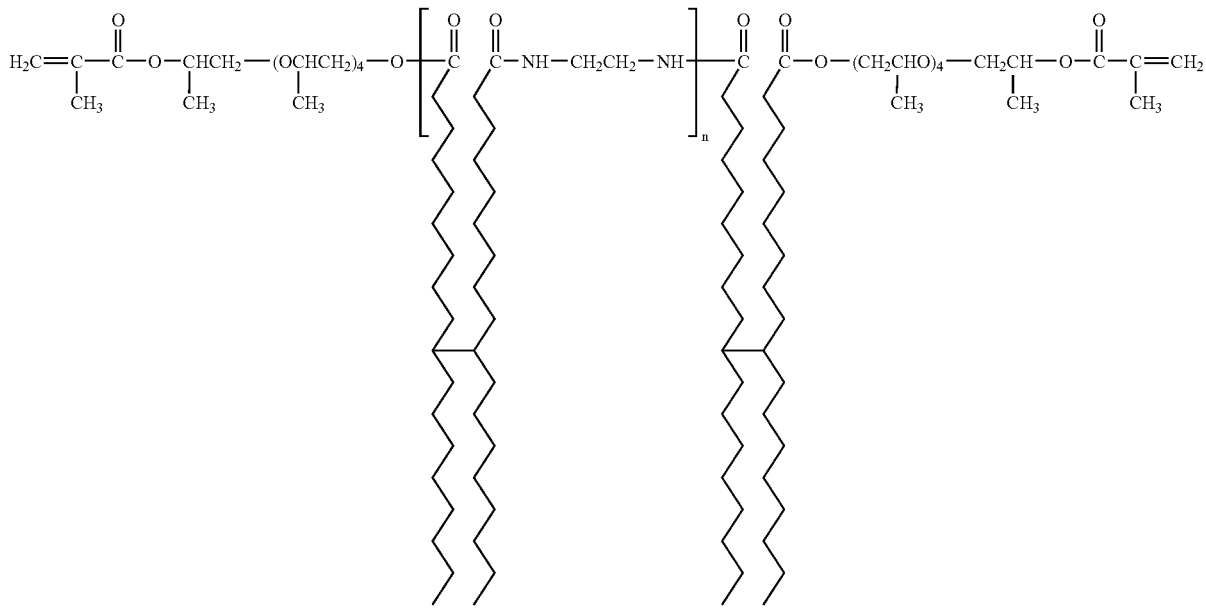

wherein n=1.

EXAMPLE V

The process of Examples I and II is repeated except that the caprolactone acrylate is replaced with an equimolar amount of 2-hydroxyethyl acrylate, available from Sigma-Aldrich Fine Chemicals. It is believed that the product will be of the formula

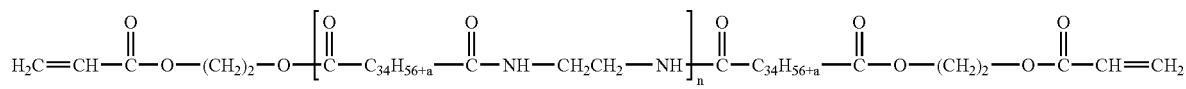

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12 and n is 1, including (but not limited to) isomers of the formula

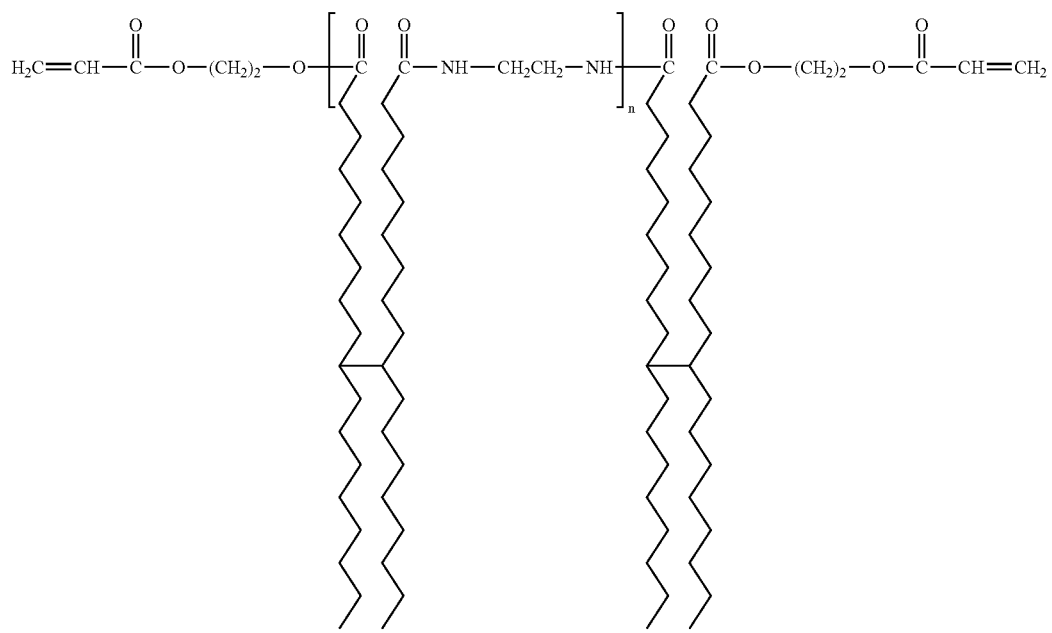

wherein n is 1.

EXAMPLE VI

The process of Examples I and II is repeated except that the caprolactone acrylate is replaced with an equimolar amount of 1,4-butanedial vinyl ether, available from Sigma-Aldrich Fine Chemicals, Milwaukee, Wis. It is believed that the product will be of the formula

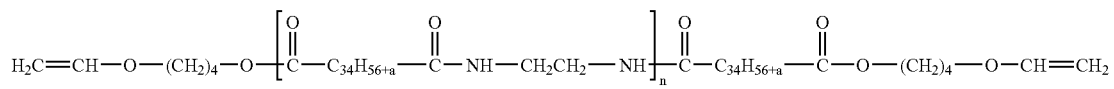

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11 or 12 and n is 1, including (but not limited to) isomers of the formula

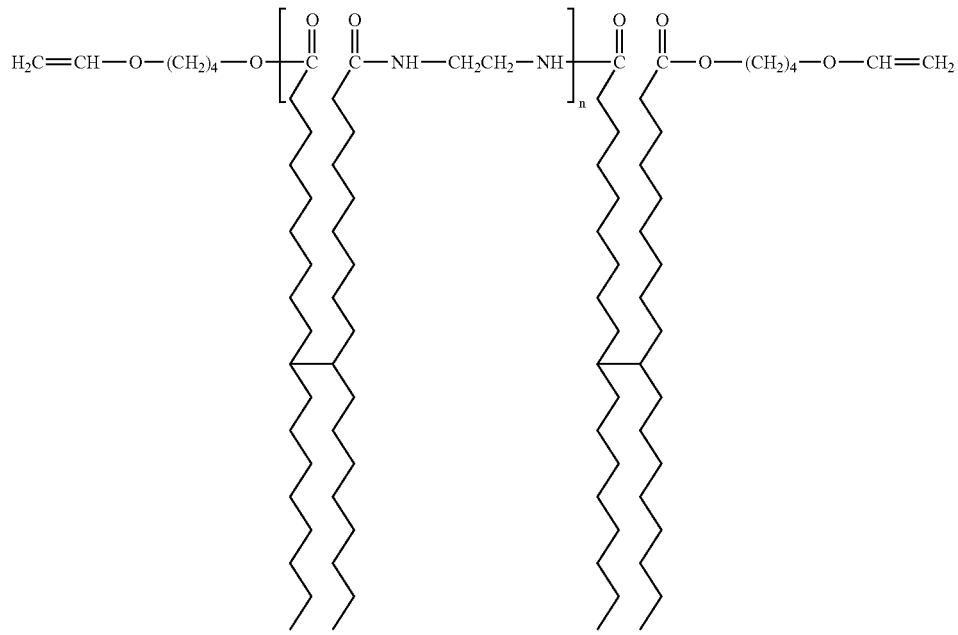

wherein n is 1.

EXAMPLE VII

The process of Examples I and II is repeated except that the caprolactone acrylate is replaced with an equimolar amount of di(ethyleneglycol)vinyl ether, available from Sigma-Aldrich Fine Chemicals, Milwaukee, Wis. It is believed that the product will be of the formula

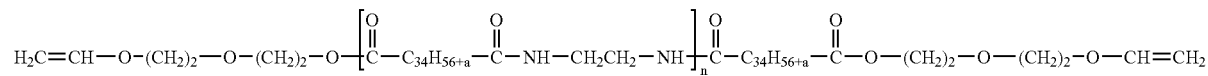

wherein $-C_{34}H_{56+a}-$ represents a branched alkylene group which may include unsaturations and cyclic groups, wherein a is an integer of 0, 1, 2, 3, 4, 5, 6, 7, 8, 9, 10, 11, or 12 and n is 1, including (but not limited to) isomers of the formula

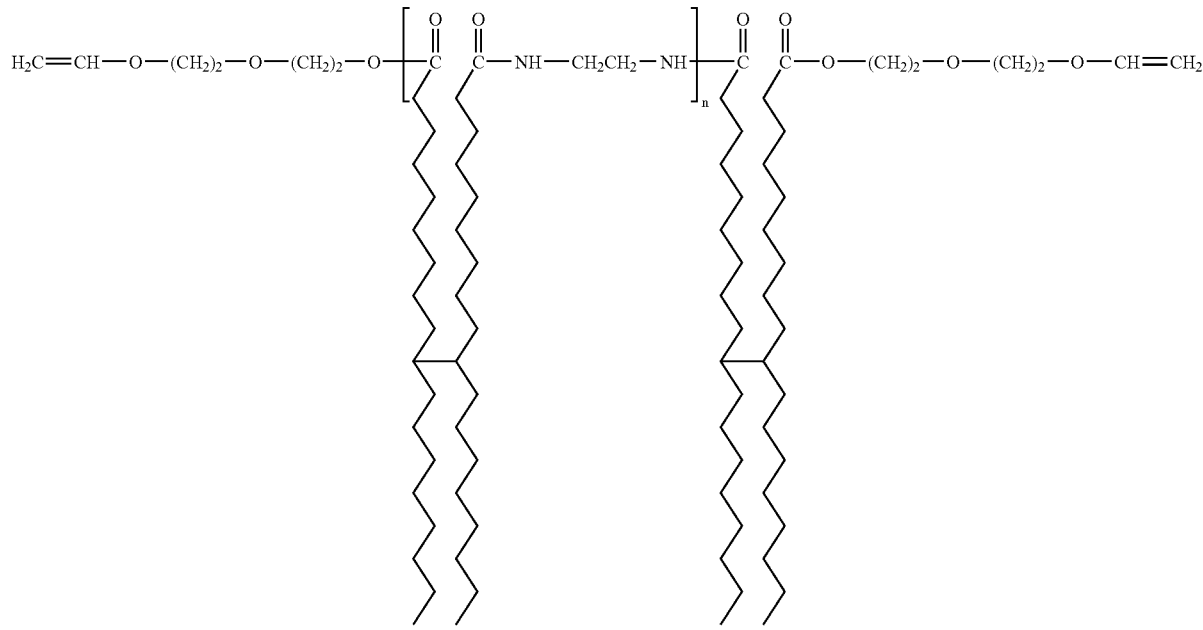

wherein n is 1.

GPC Results

The molecular weight (weight average and number average) of some of the compounds thus prepared were measured by elution in THF through five Waters Styragel columns: HR1, HR3, HR4, HR5, HR6. The column set was calibrated against polystyrene and the molecular weights were expressed as polystyrene molecular weight equivalents. The solvent pumping system was a Waters Model 2695, and detection was provided by a Waters Model 410 refractive index detector. The results are shown in the table below:

|  | $M_n$ (×1000) | $M_w$ (×1000) | $P_d$ ($M_w/M_n$) |
|---|---|---|---|
| Example II | 2.4 | 3.6 | 1.50 |

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A process for preparing a compound of the formula

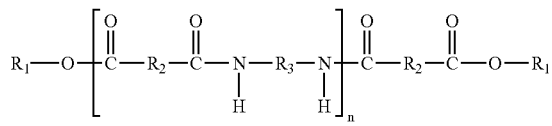

wherein $R_1$ is (i) an alkyl group having at least one ethylenic unsaturation therein, including linear and branched, cyclic and acyclic, and substituted and unsubstituted alkyl groups, and wherein hetero atoms either may or may not be present in the alkyl group, (ii) an arylalkyl group having at least one ethylenic unsaturation therein, including substituted and unsubstituted arylalkyl groups, wherein the alkyl portion of the arylalkyl group can be linear or branched, cyclic or acyclic, and substituted or unsubstituted, and wherein hetero atoms either may or may not be present in either the aryl or the alkyl portion of the arylalkyl group, or (iii) an alkylaryl group having at least one ethylenic unsaturation therein, including substituted and unsubstituted alkylaryl groups, wherein the alkyl portion of the alkylaryl group can be linear or branched, cyclic or acyclic, and substituted or unsubstituted, and wherein hetero atoms either may or may not be present in either the aryl or the alkyl portion of the alkylaryl group, $R_2$ and $R_3$ each, independently of the others, are (i) alkylene groups, including linear and branched, saturated and unsaturated, cyclic and acyclic, and substituted and unsubstituted alkylene groups, and wherein hetero atoms either may or may not be present in the alkylene group, (ii) arylene groups, including substituted and unsubstituted arylene groups, and wherein hetero atoms either may or may not be present in the arylene group, (iii) arylalkylene groups, including substituted and unsubstituted arylalkylene groups, wherein the alkyl portion of the arylalkylene group can be linear or branched, saturated or unsaturated, cyclic or acyclic, and substituted or unsubstituted, and wherein hetero atoms either may or may not be present in either the aryl or the alkyl portion of the arylalkylene group, or (iv) alkylarylene groups, including substituted and unsubstituted alkylarylene groups, wherein the alkyl portion of the alkylarylene group can be linear or branched, saturated or unsaturated, cyclic or acyclic, and substituted or unsubstituted, and wherein hetero atoms either may or may not be present in either the aryl or the alkyl portion of the alkylarylene group, and n is an integer representing the number of repeat amide units and is at least 1, said process comprising: (a) reacting a diacid of the formula

HOOC—$R_2$—COOH with a diamine of the formula $$\begin{array}{c} H \\ \diagdown \\ N-R_3-N \\ \diagup \quad\quad \diagdown \\ H \quad\quad\quad H \end{array} \begin{array}{c} H \\ \diagup \\ \\ \\ \end{array}$$

in the absence of a solvent while removing water from the reaction mixture to form an acid-terminated oligoamide intermediate of the formula $$HO \left[ \begin{array}{c} O \\ \| \\ C-R_2-C \\ \| \\ O \end{array} - \begin{array}{c} \\ N-R_3-N \\ | \quad\quad | \\ H \quad\quad H \end{array} \right]_n \begin{array}{c} O \\ \| \\ C-R_2-C-OH; \\ \| \\ O \end{array}$$

and (b) reacting the acid-terminated oligoamide intermediate with a monoalcohol of the formula $R_1$—OH in the presence of a coupling agent and a catalyst to form the product of the formula $$R_1-O \left[ \begin{array}{c} O \\ \| \\ C-R_2-C \\ \| \\ O \end{array} - \begin{array}{c} \\ N-R_3-N \\ | \quad\quad | \\ H \quad\quad H \end{array} \right]_n \begin{array}{c} O \\ \| \\ C-R_2-C-O-R_1. \\ \| \\ O \end{array}$$

2. A process according to claim 1 wherein about n+1 molar equivalents of the diacid and from about 0.75 n to about 1.5 n molar equivalents of the diamine are reacted to form the oligoamide intermediate.

3. A process according to claim 1 wherein the reaction between the diacid and the diamine to form the oligoamide intermediate is carried out at a temperature of at least about 130° C., and wherein the reaction between the diacid and the diamine to form the oligoamide intermediate is carried out at a temperature of no more than about 180° C.

4. A process according to claim 1 wherein the reaction between the diacid and the diamine to form the oligoamide intermediate is carried out for at least about 2 hours.

5. A process according to claim 1 wherein the coupling agent is 1,3-dicyclohexylcarbodiimide, 1-[3-(dimethylamino)propyl]3-ethylcarbodiimide HCl, N,N-carbonyldiimidazole, N-cyclohexyl-N'-(2-morpholinoethyl)-carbodiimide methyl-p-toluenesulfonate, (benzotriazol-1-yloxy)tris(dimethylamino)phosphonium hexafluorophosphate, (o-benzotriazol-1-yl)-N,N,N',N'-bis(tetramethylene)uronium hexafluorophosphate, bis(2-oxo-3-oxazolidinyl)phosphonic chloride, (1H-1,2,3-benzotriazol-1-yloxy)tris(pyrrolidino)phosphonium hexafluorophosphate, or mixtures thereof.

6. A process according to claim 1 wherein the catalyst is 4-dimethylaminopyridine, triethylamine, 1,8-diazabicyclo[5.4.0]undec-7-ene, or mixtures thereof.

7. A process according to claim 1 wherein the oligoamide intermediate and the monoalcohol are present in relative amounts of at least about 2 moles of monoalcohol per every 1 mole of oligoamide intermediate.

8. A process according to claim 1 wherein the oligoamide intermediate and the coupling agent are present in relative amounts of at least about 1.8 moles of coupling agent per every 1 mole of oligoamide intermediate.

9. A process according to claim 1 wherein the oligoamide intermediate and the catalyst are present in relative amounts of at least about 0.05 mole of catalyst per every 1 mole of oligoamide intermediate.

10. A process according to claim 1 wherein the reaction between the oligoamide intermediate and the monoalcohol is carried out at a temperature of at least about 15° C., and wherein the reaction between the oligoamide intermediate and the monoalcohol is carried out at a temperature of no more than about 50° C.

11. A process according to claim 1 wherein the reaction between the oligoamide intermediate and the monoalcohol is carried out for a period of at least about 2.5 hours.

12. A process according to claim 1 wherein $R_1$ is an alkyl group having at least one ethylenic unsaturation therein, including linear and branched, cyclic and acyclic, and substituted and unsubstituted alkyl groups, and wherein hetero atoms either may or may not be present in the alkyl group.

13. A process according to claim 12 wherein the alkyl group is an unsubstituted alkyl group.

14. A process according to claim 1 wherein $R_1$ is of the formula $H_2C$=$CH$—$O$—$(CH_2)_4$—, $H_2C$=$CH$—$O$—$(CH_2)_2$—$O$—$(CH_2)_2$—, $$H_2C=CH-\overset{\overset{O}{\|}}{C}-O-(CH_2)_2-,$$

$$H_2C=CH-\overset{\overset{O}{\|}}{C}-O-(CH_2)_2-\left[O-\overset{\overset{O}{\|}}{C}-(CH_2)_5\right]_2-,$$

$$H_2C=\underset{\underset{CH_3}{|}}{C}-\overset{\overset{O}{\|}}{C}-O-\underset{\underset{CH_3}{|}}{CHCH_2}-(O\underset{\underset{CH_3}{|}}{CHCH_2})_4-, \text{ or}$$

$$H_2C=\underset{\underset{CH_3}{|}}{C}-\overset{\overset{O}{\|}}{C}-O-(CH_2)_2-\left[O-(CH_2)_2\right]_m-$$

wherein m is an integer representing the number of repeating [O—$(CH_2)_2$] units.

15. A process according to claim 1 wherein $R_2$ is an alkylene group, including linear and branched, saturated and unsaturated, cyclic and acyclic, and substituted and unsubstituted alkylene groups, and wherein hetero atoms either may or may not be present in the alkylene group.

16. A process according to claim 15 wherein the alkylene group is a saturated unsubstituted alkylene group.

17. A process according to claim 1 wherein $R_2$ is an alkylene group of the formula $-C_{34}H_{56+a}-$ and are branched alkylene groups which may include unsaturations and cyclic groups, wherein a is an integer of 0, 1, 2, 3, 4, 5, 6, 7, 8, 9, 10, 1, or 12.

18. A process according to claim 17 wherein $R_2$ includes isomers of the formula

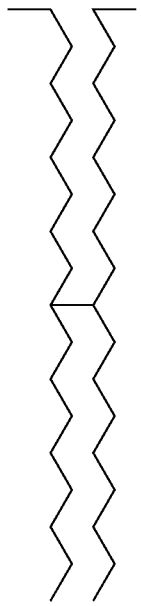

19. A process according to claim 1 wherein $R_3$ is an alkylene group, including linear and branched, saturated and unsaturated, cyclic and acyclic, and substituted and unsubstituted alkylene groups, and wherein hetero atoms either may or may not be present in the alkylene group.

20. A process according to claim 19 wherein the alkylene group is a saturated unsubstituted alkylene group.

21. A process according to claim 1 wherein $R_3$ is a $-CH_2CH_2-$ group.

22. A process according to claim 1 wherein n is no more than about 20.

23. A process according to claim 1 wherein n is 1 or 2.

24. A process according to claim 1 wherein the compound is of the formula

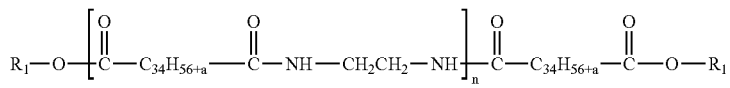

wherein $-C_{34}H_{56+a}-$ represents a branched alkylene group which may include unsaturations and cyclic groups, wherein a is an integer of 0, 1, 2, 3, 4, 5, 6, 7, 8, 9, 10, 11, or 12 and wherein n is 1 or 2.

25. A process according to claim 1 wherein the compound is of the formula

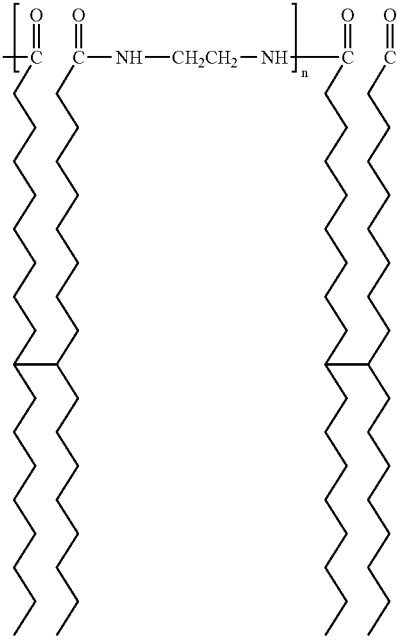

26. A process according to claim 1 wherein the compound is of the formula

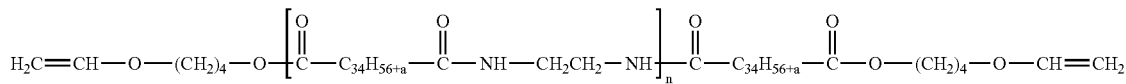
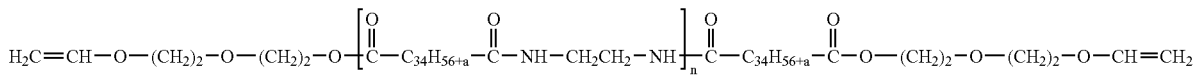
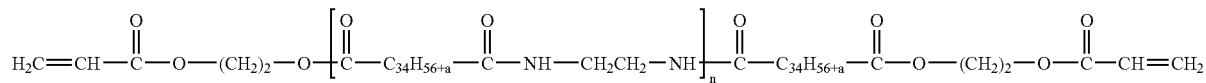
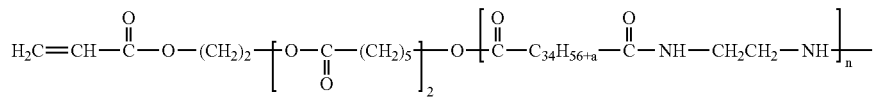
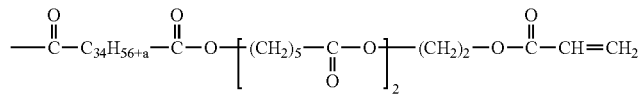
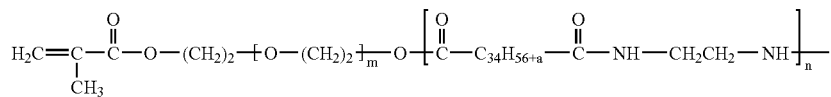
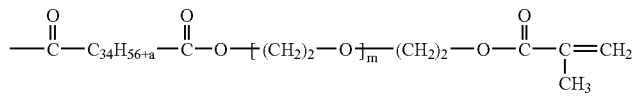
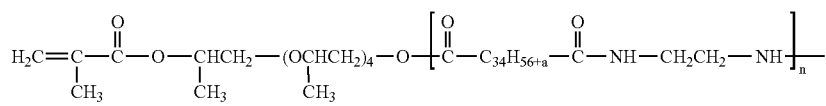
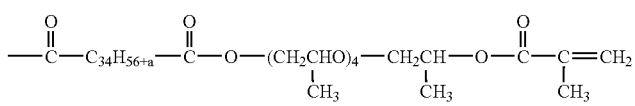
or mixtures thereof, wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, n is 1 or 2, and m is an integer representing the number of repeating [O—$(CH_2)_2$] units.

27. A process according to claim 1 wherein the compound is of the formula
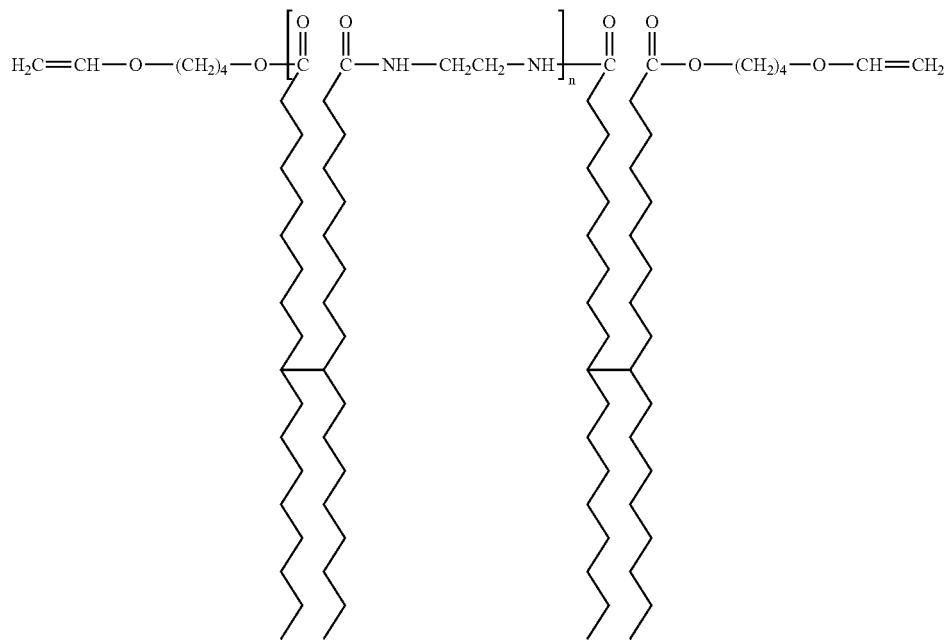
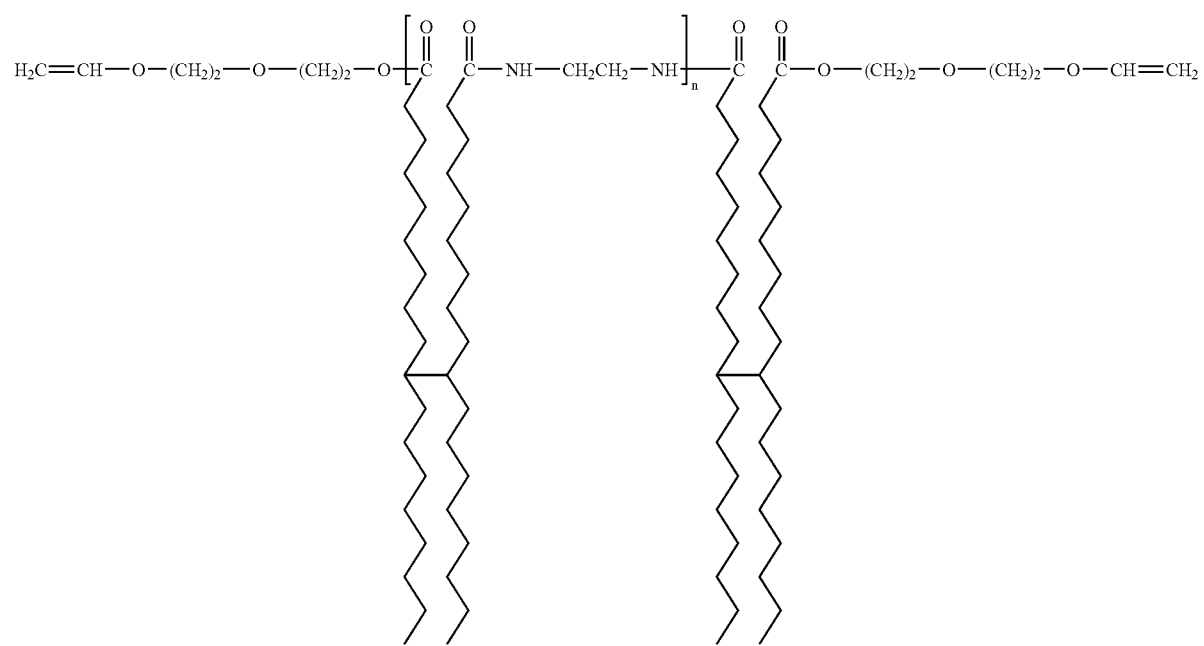

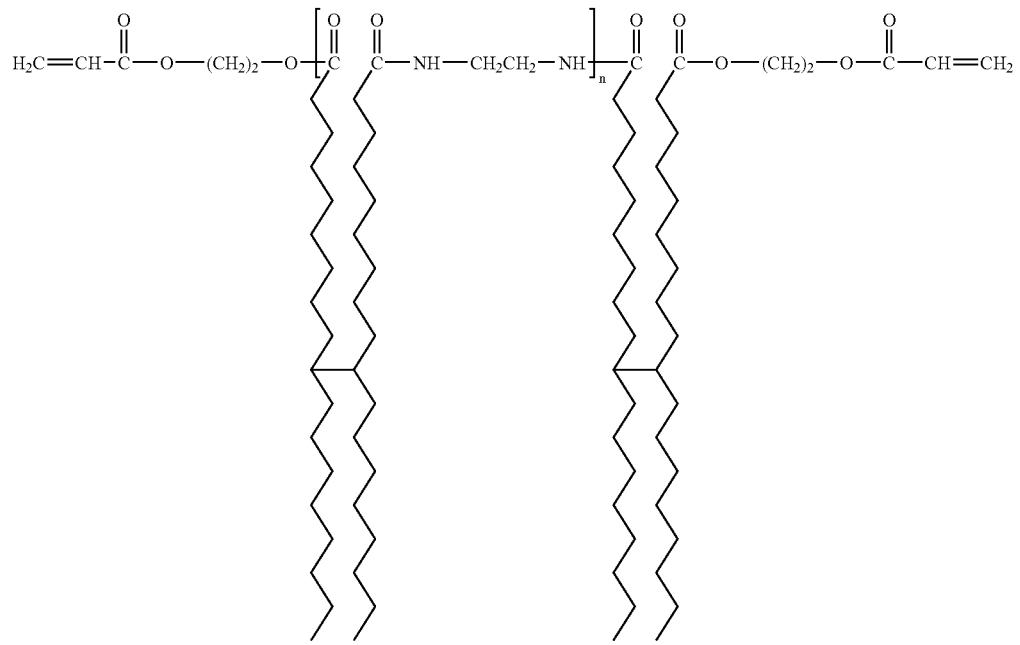
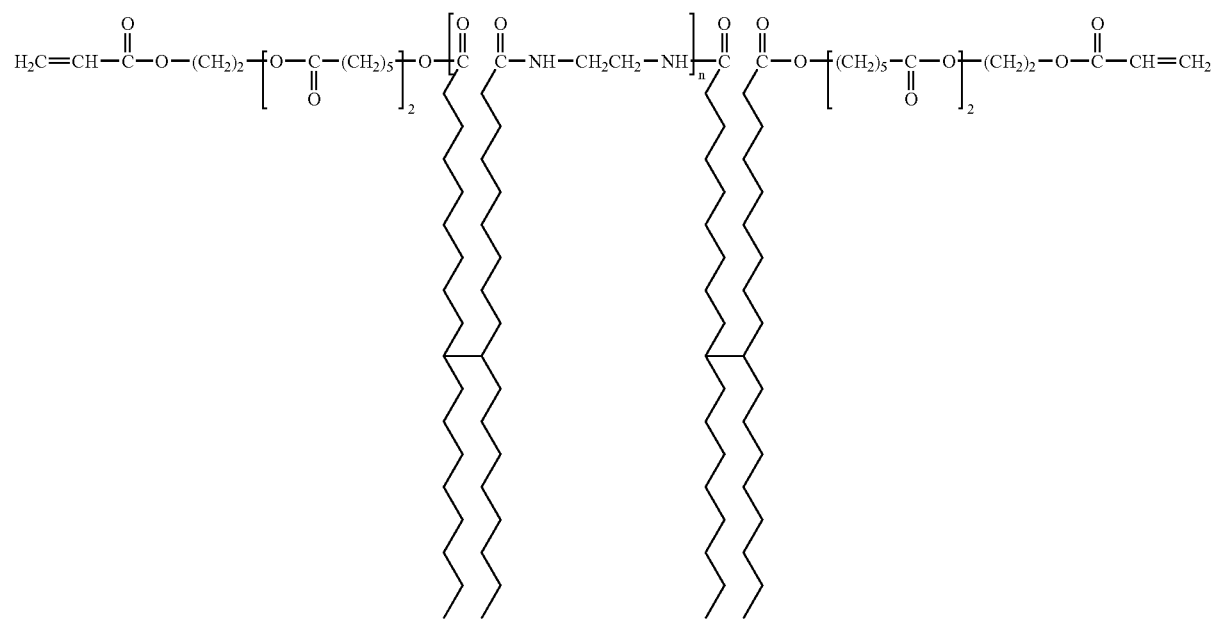

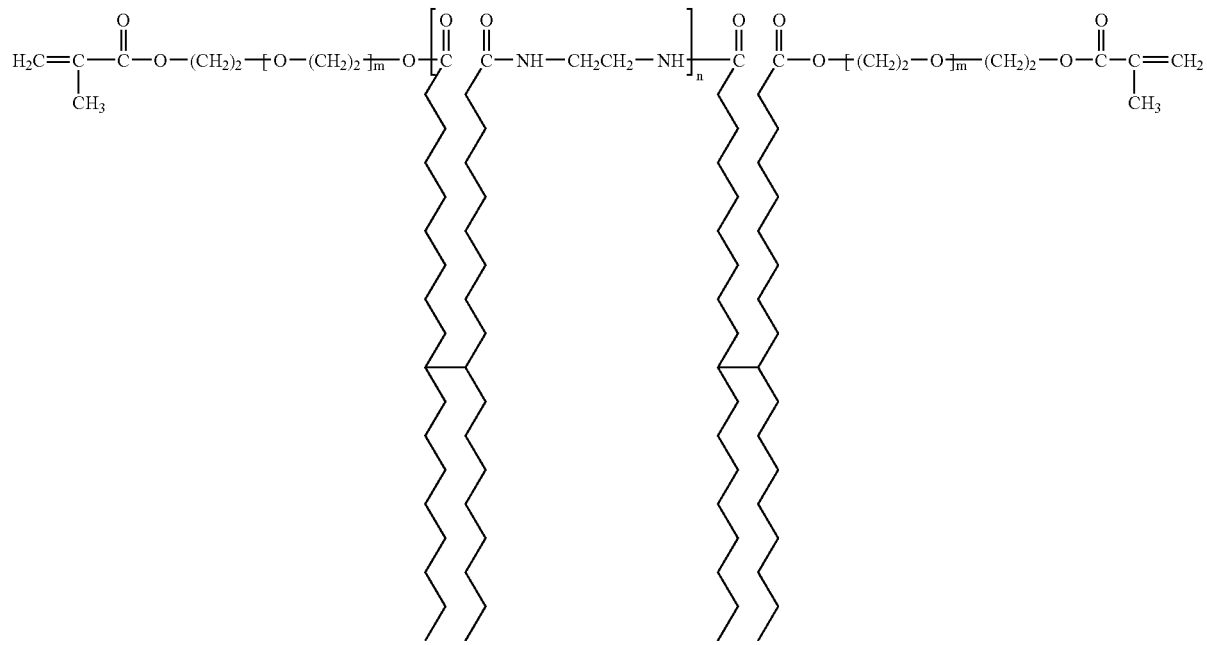
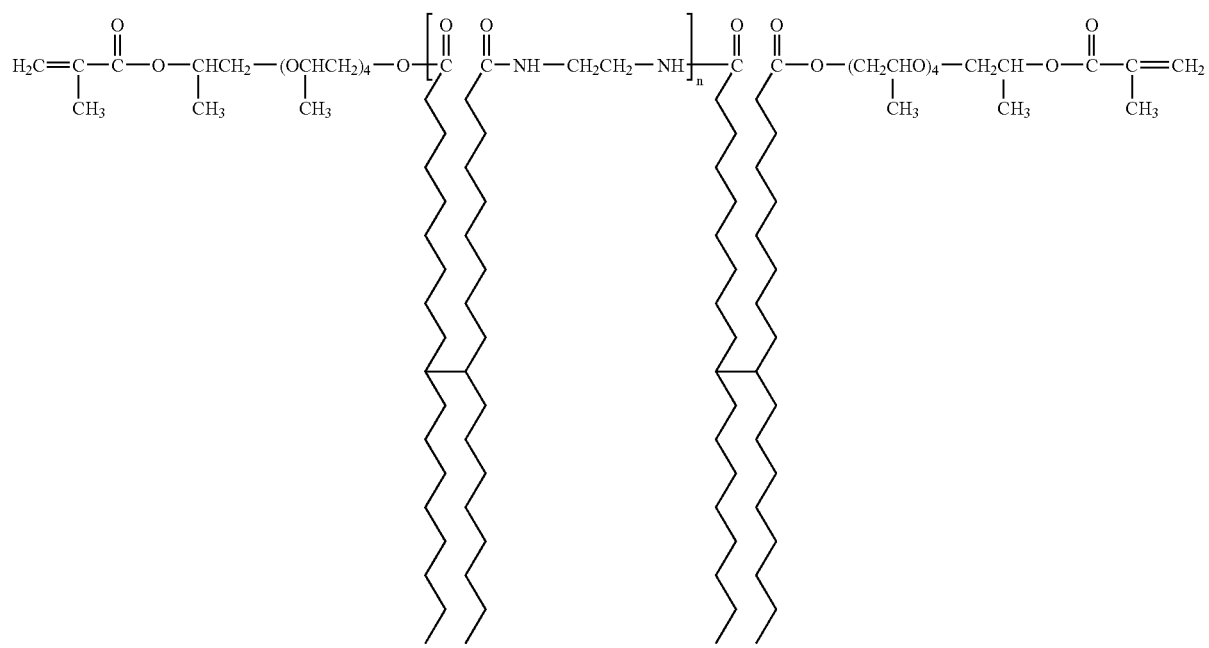
or mixtures thereof, wherein n is 1 or 2 and m is an integer representing the number of repeating [O—(CH$_2$)$_2$] units.
* * * * *